(12) United States Patent
Nilsson et al.

(10) Patent No.: US 7,785,589 B2
(45) Date of Patent: Aug. 31, 2010

(54) ANTIBODIES AGAINST A PEPTIDE EPITOPE OF APOLIPOPROTEIN B

(75) Inventors: Jan Nilsson, Genarp (SE); Prediman K. Shah, Los Angeles, CA (US)

(73) Assignees: Forskarpatent I SYD, Lund (SE); Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 12/394,787

(22) Filed: Feb. 27, 2009

(65) Prior Publication Data
US 2009/0280126 A1    Nov. 12, 2009

Related U.S. Application Data

(62) Division of application No. 11/485,549, filed on Jul. 12, 2006, now Pat. No. 7,537,758, which is a division of application No. 10/115,072, filed on Apr. 4, 2002, now abandoned.

(60) Provisional application No. 60/281,410, filed on Apr. 5, 2001.

(30) Foreign Application Priority Data

| Apr. 5, 2001 | (SE) | .................................... 0101232 |
| Nov. 9, 2001 | (SE) | .................................... 0103754 |

(51) Int. Cl.
C07K 4/12      (2006.01)
C07K 16/18     (2006.01)
A61K 39/395    (2006.01)

(52) U.S. Cl. .................. 424/130.1; 424/139.1; 514/2; 530/326; 530/387.1; 530/387.9

(58) Field of Classification Search .................... None
See application file for complete search history.

(56) References Cited

U.S. PATENT DOCUMENTS

| 4,970,144 | A | 11/1990 | Fareed et al. |
| 5,408,038 | A | 4/1995 | Smith et al. |
| 5,827,516 | A | 10/1998 | Urban et al. |
| 5,861,276 | A | 1/1999 | Kwak et al. |
| 5,972,890 | A | 10/1999 | Lees et al. |
| 2004/0002111 | A1 | 1/2004 | Hansson et al. |

FOREIGN PATENT DOCUMENTS

| EP | 0911344 A1 | 4/1999 |
| EP | 1186299 A1 | 3/2002 |
| WO | 93/18067 A1 | 9/1993 |
| WO | 94/00592 A1 | 1/1994 |
| WO | 97/43311 A1 | 11/1997 |
| WO | 98/13385 A2 | 4/1998 |
| WO | 98/42751 A1 | 10/1998 |
| WO | 98/56938 A1 | 12/1998 |
| WO | 9908109 | 2/1999 |
| WO | 9918986 | 4/1999 |
| WO | 00/02920 A1 | 1/2000 |
| WO | 01/32070 A2 | 5/2001 |
| WO | 01/64008 A2 | 9/2001 |
| WO | 01/68119 A1 | 9/2001 |
| WO | 02/06314 A2 | 1/2002 |
| WO | 03/007689 A2 | 1/2003 |

OTHER PUBLICATIONS

Schiopu et al. Recombinant human antibodies against aldehyde-modified apolipoprotein B-100 peptide sequences inhibit atherosclerosis. Circulation 110: 2047-2052, 2004.*
Pease et al. Use of bacterial expression cloning to localize the epitopes for a series of monoclonal antibodies against apolipoprotein B100. J Biol Chem 265(1): 553-568, 1990.*
Milne et al. The use of monoclonal antibodies to localize the low density lipoprotein receptor-binding domain of apolipoprotein B. J Biol Chem 264(33): 19754-19760, 1989.*
Wang et al. Well-defined regions of apolipoprotein B-100 undergo conformation change during its intravascular metabolism. Arterioscler Thromb Vasc Biol 20: 1301-1308, 2000.*
Skolnick et al., "From genes to protein structure and function: novel applications of computational approaches in the genomic era"; Trends in Biotech, Jan. 2000, vol. 18.; pp. 34-39.
Peer Bork; "Powers and Pitfalls in sequence Analysis: The 70% Hurdle"; Genome Research; Cold Spring Harbor Laboratory Press, 2000, pp. 398-400.
Doerks et al., "Protein annotation: detective work for function prediction"; Trends in Genetics; Jun. 1998, vol. 14, No. 6, pp. 248-250.
Smith et al., "The challenges of genome sequence annotation of "The devil is in the details""; Nature Biotechnology; Nov. 1997, vol. 15, pp. 1222-1223.
George et al., "Hyperimmunization of apo-E-deficient mice with homologous malondialdehyde low-density lipoprotein suppresses early atherogenesis"; Atherosclerosis; 1998, vol. 138; pp. 147-152.
Palinski et al., "Immunization of low density lipoprotein (LDL) receptor-deficient rabbits with homologous malondialdehyde-modified LDL reduces atherogenesis"; Proc. Natl. Acad. Sci. USA, Jan. 1995, vol. 92, pp. 821-825.
Fredrikson et al., "Identivication of Immune Responses Against Aldehyde-Modified Peptide Sequences in ApoB Associated With Cardiovascular Disease"; Arterioscler Thromb Vasc. Biol.; May 2003; pp. 872-878.
Fredrikson et al., "Inhibition of Atherosclerosis in ApoE-Null Mice by Immunization with ApoB-100 Peptide Sequences"; Arterioscler Thromb Vasc. Biol.; May 2003; pp. 879-884.
Fredrikson et al., "Atheroproctective Immunization with MDA-modified apo B-100 peptide sequences is associated with activation of Th2 specific antibody expression"; Autoimmunity, Mar. 2005; vol. 38, No. 2; pp. 171-179.

(Continued)

*Primary Examiner*—Bridget E Bunner
(74) *Attorney, Agent, or Firm*—Gauthier & Connors LLP

(57) ABSTRACT

The present invention relates to antibodies raised against fragments of apolipoprotein B, in particular defined peptides thereof, for immunization or therapeutic treatment of mammals, including humans, against ischemic cardiovascular diseases, using one or more of such antibodies.

11 Claims, 6 Drawing Sheets

OTHER PUBLICATIONS

Goldberg et al., "The NH2-terminal Region of Apolipoprotein B Is Sufficient for Lipoprotein Association with Glycosaminoglycans"; The Journal of Biological Chemistry; Dec. 1998; vol. 273, No. 52; pp. 32355-35361.

Goncalves et al., "Humoral Immune Response Against Defined Oxidized Low-Density Lipoprotein antigens Reflects Structure and Disease Activity of Carotid Plaques"; Arterioscler Thromb Vasc. Biol.; 2005, pp. 1250-1255.

Ameli et al., "Effect of Immunization With Homologous LDK and oxidized LDL on Early Atherosclerosis in Hypercholesterolemic Rabbits"; Arteriosclerosis, Thrombosis, and Vascular Biology; 1996; pp. 1074-1079.

Steven E. Brenner; "Errors in genome annotation"; Trends in Genetics; Apr. 1999, vol. 15, No. 4, pp. 132-133.

Bork et al., "Go hunting in sequence databases but watch out for the traps"; Trends in Genetics; Oct. 1996, vol. 12, No. 10, pp. 425-427.

James A. Wells; "Additivity of Mutational Effects in Proteins"; Perspectives in Biochemistry; Sep. 1990, vol. 29, No. 37, pp. 8509-8517.

Ngo et al., "Computational Complexity, Protein Structure Prediction, and the Levinthal Paradox"; The Protein Folding Problem and Tertiary Structure Prediction; 1994. pp. 492-495.

Hammer et al., "Generation, Characterization, and Histochemical Application of Monoclonal Antibodies Selectively Recognizing Oxidatively Modified ApoB-Containing Serum Lipoproteins"; Atreriosclerosis, Thrombosis, and Vascular Biology; 1995, pp. 704-713.

Ballow et al., "Immunomodulation and Immunotherapy"; JAMA, Dec. 1997, vol. 278, No. 22, pp. 2008-2017.

Gordon P. Moore; "Genetically Engineered Antibodies"; Clincal Chemistry, 1989, vol. 35, No. 9, pp. 1849-1853.

Fredrikson et al., "Treatment with apo B peptide vaccines inhibits atherosclerosis in human apo B-100 transgenic mice without inducing an increase in peptide-specific antibodies"; Journal of Internal Medicine; 2008, pp. 563-570.

Nilsson et al., "Immunization With Homologous Oxidized Low Density Lopoprotein Reduces Neointimal Formation After Balloon Injury in Hypercholesterolemic Rabbits"; JACC, vol. 30, No. 7, Dec. 1997, pp. 1886-1891.

Freigang et al., "Immunization of LDL Receptor-Deficient Mice With Homologous Malondialdehyde-Mofidied adn Native LDL Reduces Progression of Atherosclerosis by Mechanisms Other Than Induction of High Titers of Antibodies to Oxidative Neoepitopes"; Arterioscler Thromb Vasc. Biol., Jul. 1998, p. 1972-1982.

Zhou et al., "LDL Immunization Induces T-Cell-Dependent Antibody Formation and Protection Against Atherosclerosis"; 2001, pp. 108-114.

Palinski, Wulf et al. "Antisera and Monoclonal Antibodies Specific for Epitopes Generated during Oxidative Modification of Low Density Lipoprotein" Arteriosclerosis vol. 10, No. 3; pp. 325-335; May/Jun. 1990.

Rosenfeld, Michael E. "Distribution of Oxidation Specific Lipid-Protein Adducts and Apolipoprotein B in Atherosclerotic Lesions of Varying Severity from WHHL Rabbits" Arteriosclerosis vol. 10, No. 3; pp. 326-349; May/Jun. 1990.

Lefvert, A.K. "Heterogeneity of autoantibodies against cardiolipin and oxidatively modified LDLs revealed by human monoclonal antibodies" Journal of Internal Medicine 2000: 247; pp. 285-390.

Dunning, Allison et al. "Association between epitopes detected by monclonal antibody BIP and the XbaI polymorphism of Apolipoprotein B" Clinical Genetics 1988: 33: pp. 181-188.

Chen, San-Hwan et al. "Apolipoprotein B-48 Is the Product of a Messenger RNA with an Organ-Specific In-Frame Stop Codon." Science, vol. 238 1987; pp. 363-366.

Young, Stephen G. et al. "Definition of a nonlinear conformational epitope for the apolipoprotein B-100-specific monoclonal antibody, MB47." Journal of Lipid Research; vol. 35; pp. 399-407; 1994.

Fredrikson, Gunilla Nordin et al. "Immunzation of atherosclerosis in apo E null mice by immunization with native and MDA-modified apo B peptide sequences" Journal of the American College of Cardiology, Elsevier, New York, NY, US; vol. 39, No. 5; Supplement A; p. 240A; Mar. 2002.

Knott, T.C. et al. "RecName:Full=Apolipoprotein B-100; Short=Apo B-100; Contains: RecName: Full=Apolipoprotein B-48; Short=Apo B-48; Flags: Precursor" UNIPROT, Jan. 11, 2001.

\* cited by examiner

ANTIBODIES AGAINST A PEPTIDE EPITOPE OF APOLIPOPROTEIN B

PRIORITY INFORMATION

This application is a divisional of U.S. patent application Ser. No. 11/485,549, filed on Jul. 12, 2006 which is a divisional of U.S. Utility application Ser. No. 10/115,072, filed Apr. 4, 2002, now abandoned, which claims priority to Swedish Application Nos. 0101232-7, filed on Apr. 5, 2001, and 0103754-8, filed Nov. 9, 2001, and the benefit of U.S. Provisional Application Ser. No. 60/281,410, filed Apr. 5, 2001, the content of which is incorporated herein by reference.

BACKGROUND OF THE INVENTION

1. Field of the Invention

The present invention relates to new peptides, in particular peptides to be used for immunization therapy for treatment of atherosclerosis, and for development of peptide based ELISA for the determination of immune response against oxidized low density lipoprotein and the diagnosis of the presence or absence of atherosclerosis.

2. Brief Description of the Art

In particular the invention includes:
1) The use of any of the peptides listed in table 1, alone or in combination, native or MDA-modified, preferably together with a suitable carrier and adjuvant as an immunotherapy or "anti-atherosclerosis "vaccine" for prevention and treatment of ischemic
2) cardiovascular disease.
3) The use of the same peptides in ELISA for detection of antibodies related to increased or decreased risk of development of ischemic cardiovascular diseases.

Atherosclerosis is a chronic disease that causes a thickening of the innermost layer (the intima) of large and medium-sized arteries. It decreases blood flow and may cause ischemia and tissue destruction in organs supplied by the affected vessel. Atherosclerosis is the major cause of cardiovascular disease including myocardial infarction, stroke and peripheral artery disease. It is the major cause of death in the western world and is predicted to become the leading cause of death in the entire world within two decades.

The disease is initiated by accumulation of lipoproteins, primarily low-density lipoprotein (LDL), in the extracellular matrix of the vessel. These LDL particles aggregate and undergo oxidative modification. Oxidized LDL is toxic and cause vascular injury. Atherosclerosis represents in many respects a response to this injury including inflammation and fibrosis.

In 1989 Palinski and coworkers identified circulating autoantibodies against oxidized LDL in humans. This observation suggested that atherosclerosis may be an autoimmune disease caused by immune reactions against oxidized lipoproteins. At this time several laboratories began searching for associations between antibody titers against oxidized LDL and cardiovascular disease. However, the picture that emerged from these studies was far from clear. Antibodies existed against a large number of different epitopes in oxidized LDL, but the structure of these epitopes was unknown. The term "oxidized LDL antibodies" thus referred to an unknown mixture of different antibodies rather than to one specific antibody. T cell-independent IgM antibodies were more frequent than T-cell dependent IgG antibodies.

Antibodies against oxidized LDL were present in both patients with cardiovascular disease and in healthy controls. Although some early studies reported associations between oxidized LDL antibody titers and cardiovascular disease, others were unable to find such associations. A major weakness of these studies was that the ELISA tests used to determine antibody titers used oxidized LDL particles as ligand. LDL composition is different in different individuals, the degree of oxidative modification is difficult both to control and assess and levels of antibodies against the different epitopes in the oxidized LDL particles can not be determined. To some extent, due to the technical problems it has been difficult to evaluate the role of antibody responses against oxidized LDL using the techniques available so far, but, however, it is not possible to create well defined and reproducible components of a vaccine if one should use intact oxidized LDL particles.

Another way to investigate the possibility that autoimmune reactions against oxidized LDL in the vascular wall play a key role in the development of atherosclerosis is to immunize animals against its own oxidized LDL. The idea behind this approach is that if autoimmune reactions against oxidized LDL are reinforced using classical immunization techniques this would result in increased vascular inflammation and progressive of atherosclerosis. To test this hypothesis rabbits were immunized with homologous oxidized LDL and then induced atherosclerosis by feeding the animals a high-cholesterol diet for 3 months.

However, in contrast to the original hypothesis immunization with oxidized LDL had a protective effect reducing atherosclerosis with about 50%. Similar results were also obtained in a subsequent study in which the high-cholesterol diet was combined with vascular balloon-injury to produce a more aggressive plaque development. In parallel with our studies several other laboratories reported similar observations. Taken together the available data clearly demonstrates that there exist immune reactions that protect against the development of atherosclerosis and that these involves autoimmunity against oxidized LDL.

These observations also suggest the possibility of developing an immune therapy or "vaccine" for treatment of atherosclerosis-based cardiovascular disease in man. One approach to do this would be to immunize an individual with his own LDL after it has been oxidized by exposure to for example copper. However, this approach is complicated by the fact that it is not known which structure in oxidized LDL that is responsible for inducing the protective immunity and if oxidized LDL also may contain epitopes that may give rise to adverse immune reactions.

The identification of epitopes in oxidized LDL is important for several aspects:

First, one or several of these epitopes are likely to be responsible for activating the anti-atherogenic immune response observed in animals immunized with oxidized LDL. Peptides containing these epitopes may therefore represent a possibility for development of an immune therapy or "atherosclerosis vaccine" in man. Further, they can be used for therapeutic treatment of atheroschlerosis developed in man.

Secondly, peptides containing the identified epitopes can be used to develop ELISAs able to detect antibodies against specific structure in oxidized LDL. Such ELISAs would be more precise and reliable than ones presently available using oxidized LDL particles as antigen. It would also allow the analyses of immune responses against different epitopes in oxidized LDL associated with cardiovascular disease.

U.S. Pat. No. 5,972,890 relates to a use of peptides for diagnosing atherosclerosis. The technique presented in said US patent is as a principle a form of radiophysical diagnosis. A peptide sequence is radioactively labeled and is injected into the bloodstream. If this peptide sequence should be identical with sequences present in apolipoprotein B it will bind to the tissue where there are receptors present for apolipoprotein B. In vessels this is above all atherosclerotic plaque. The concentration of radioactivity in the wall of the vessel can then be determined e.g., by means of a gamma camera. The technique is thus a radiophysical diagnostic method based on that radioactively labeled peptide sequences will bound to their normal tissue receptors present in atherosclerotic plaque and are detected using an external radioactivity analysis. It is a direct analysis method to identify atherosclerotic plaque. It requires that the patient be given radioactive compounds.

SUMMARY OF THE INVENTION

The technique of the present invention is based on quite different principles and methods. In accordance with claim 1 the invention relates to fragments of apolipoprotein B for immunization against cardiovascular disease as well as a method for diagnosing immuno reactions against peptide sequences of apolipoprotein B. Such immuno reactions have in turn showed to be increased in individuals having a developed atherosclerosis. The present technique is based in attaching peptide sequences in the bottom of polymer wells. When a blood sample is added the peptides will bind antibodies, which are specific to these sequences. The amount of antibodies bound is then determined using an immunological method/technique. In contrast to the technique of said US patent this is thus not a direct determination method to identify and localize atherosclerotic plaque but determines an immunological response, which shows a high degree of co-variation with the extension of the atherosclerosis.

The basic principle of the present invention is thus quite different from that of said patent. The latter depends on binding of peptide sequences to the normal receptors of the lipoproteins present in atherosclerotic tissue, while the former is based on the discovery of immuno reactions against peptide sequences and determination of antibodies to these peptide sequences.

Published studies (Palinski et al., 1995, and George et al., 1998) have shown that immunization against oxidized LDL reduces the development of atherosclerosis. This would indicate that immuno reactions against oxidized LDL in general have a protecting effect. The results given herein have, however, surprisingly shown that this is not always the case. E.g., immunization using a mixture of peptides #10, 45, 154, 199, and 240 gave rise to an increase of the development of atherosclerosis. Immunization using other peptide sequences, e.g., peptide sequences #1, and 30 to 34 lacks total effect on the development of atherosclerosis. The results are surprising because they provide basis for the fact that immuno reactions against oxidized LDL, can protect against the development, contribute to the development of atherosclerosis, and be without any effect at all depending on which structures in oxidized LDL they are directed to. These findings make it possible to develop immunization methods, which isolate the activation of protecting immuno reactions. Further, they show that immunization using intact oxidized LDL could have a detrimental effect if the particles used contain a high level of structures that give rise to atherogenic immuno reactions.

WO 99/08109 relates to the use of a panel of monoclonal mouse antibodies, which bind to particles of oxidized LDL in order to determine the presence of oxidized LDL in serum and plasma. This is thus totally different from the present invention wherein a method for determining antibodies against oxidized LDL is disclosed.

U.S. Pat. No. 4,970,144 relates to a method for preparing antibodies by means of immunization using peptide sequences, which antibodies can be used for the determination of apolipoproteins using ELISA. This is thus something further quite different from the present invention.

U.S. Pat. No. 5,861,276 describes a recombinant antibody to the normal form of apolipoprotein B. This antibody is used for determining the presence of normal apolipoprotein B in plasma and serum, and for treating atherosclerosis by lowering the amount of particles of normal LDL in the circulation.

Thus in the present invention the use of antibodies are described for treating atherosclerosis. However, contrary to the U.S. Pat. No. 5,861,276, these antibodies are directed to structures present in particles of oxidized LDL and not to the normal particle of LDL. The advantage is that it is the oxidized LDL, which is supposed to give rise to the development of atherosclerosis. The use of antibodies directed to structures being specific to oxidized LDL is not described in said US patent.

Oxidation of lipoproteins, mainly LDL, in the arterial wall is believed to be an important factor in the development of atherosclerosis. Products generated during oxidation of LDL are toxic to vascular cells, cause inflammation and initiate plaque formation. Epitopes in oxidized LDL are recognized by the immune system and give rise to antibody formation. Animal experiments have shown that some of these immune responses have a protective effect against atherosclerosis. Antibodies are generally almost exclusively directed against peptide-based structures. Using a polypeptide library covering the complete sequence of the only protein present in LDL, apolipoprotein B, the epitopes have been identified in oxidized LDL that give rise to antibody formation in man. These peptide-epitopes can be used to develop ELISAs to study associations between immune responses against oxidized LDL and cardiovascular disease and to develop an immunotherapy or anti-atherosclerosis "vaccine" for prevention and treatment of ischemic cardiovascular disease.

DETAILED DESCRIPTION OF THE INVENTION

Figure 1:
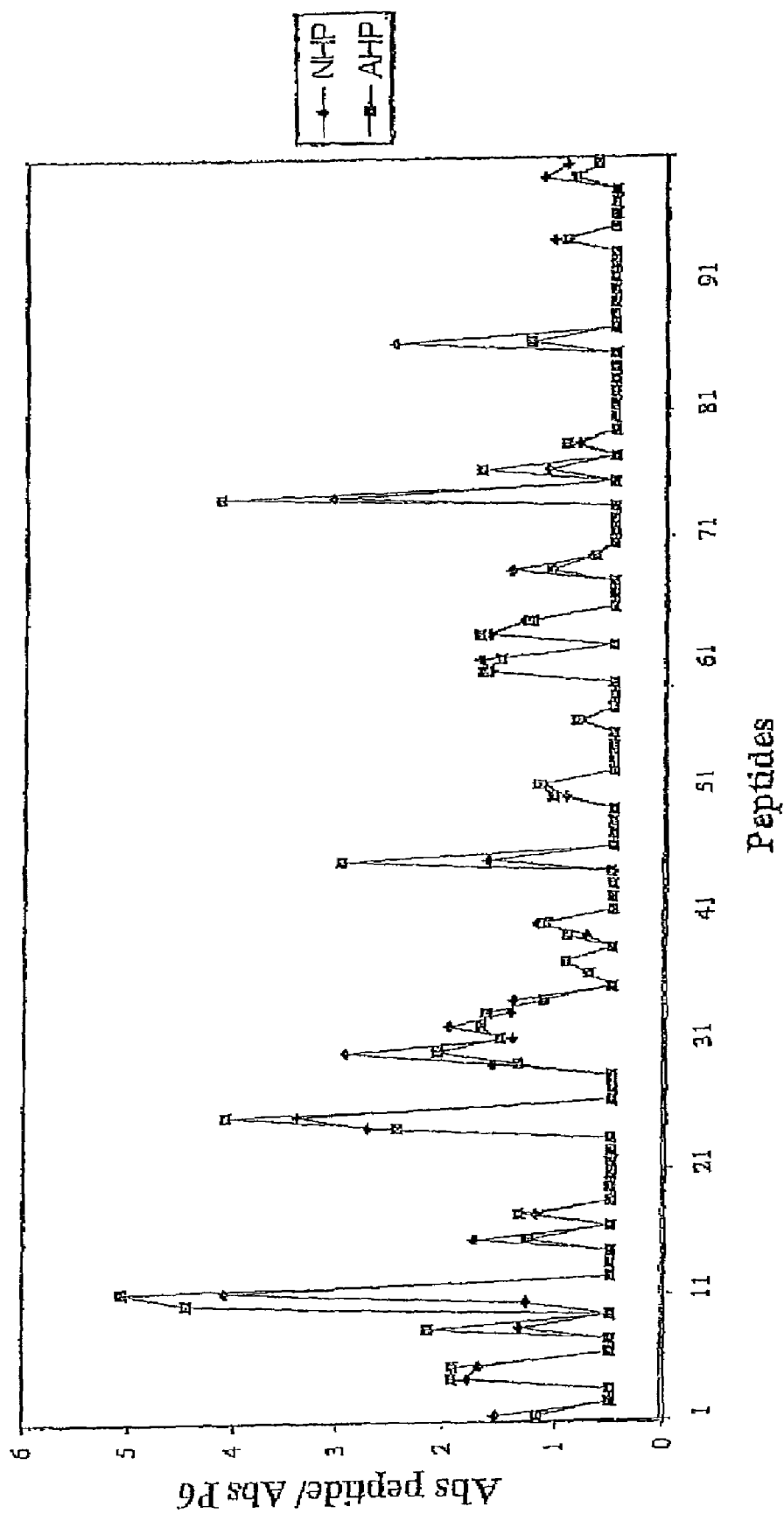
FIGS. 1-6 show antibody response to the different peptides prepared in accordance with the present invention.

A molecular characterization of the epitopes in oxidized LDL has been performed that give rise to antibody-dependent immune responses in man. The approach used takes advantage of the fact that immune reactions almost exclusively are directed against 5-6 amino acid long peptide sequences. LDL only contains one protein, the 4563 amino acid long apolipoprotein B. During oxidation apolipoprotein B is fragmented and aldehyde adducts coupled to positively charged amino acids, in particularly lysine. This means that peptide sequences not normally exposed because of the three dimensional structure of apolipoprotein B become accessible to immune cells and/or that normally exposed peptide sequences becomes immunogenic because haptenization with aldehydes.

It has thereby been determined that the following peptides, native or MDA derivatives possess such an efficiency as producing an immuno-response. These peptides are:

| | |
|---|---|
| FLDTVYGNCSTHFTVKTRKG, | (SEQ ID NO: 1) |
| PQCSTHILQWLKRVHANPLL, | (SEQ ID NO: 2) |
| VISIPRLQAEARSEILAHWS, | (SEQ ID NO: 3) |

-continued

| | |
|---|---|
| KLVKEALKESQLPTVMDFRK, | (SEQ ID NO: 4) |
| LKFVTQAEGAKQTEATMTFK, | (SEQ ID NO: 5) |
| DGSLRHKFLDSNIKFSHVEK, | (SEQ ID NO: 6) |
| KGTYGLSCQRDPNTGRLNGE, | (SEQ ID NO: 7) |
| RLNGESNLRFNSSYLQGTNQ, | (SEQ ID NO: 8) |
| SLTSTSDLQSGIIKNTASLK, | (SEQ ID NO: 9) |
| TASLKYENYELTLKSDTNGK, | (SEQ ID NO: 10) |
| DMTFSKQNALLRSEYQADYE, | (SEQ ID NO: 11) |
| MKVKIIRTIDQMQNSELQWP, | (SEQ ID NO: 12) |
| IALDDAKINFNEKLSQLQTY, | (SEQ ID NO: 13) |
| KTTKQSFDLSVKAQYKKNKH, | (SEQ ID NO: 14) |
| EEEMLENVSLVCPKDATRFK, | (SEQ ID NO: 15) |
| GSTSHHLVSRKSISAALEHK, | (SEQ ID NO: 16) |
| IENIDFNKSGSSTASWIQNV, | (SEQ ID NO: 17) |
| IREVTQRLNGEIQALELPQK, | (SEQ ID NO: 18) |
| EVDVLTKYSQPEDSLIPFFE, | (SEQ ID NO: 19) |
| HTFLIYITELLKKLQSTTVM, | (SEQ ID NO: 20) |
| LLDIANYLMEQIQDDCTGDE, | (SEQ ID NO: 21) |
| CTGDEDYTYKIKRVIGNMGQ, | (SEQ ID NO: 22) |
| GNMGQTMEQLTPELKSSILK, | (SEQ ID NO: 23) |
| SSILKCVQSTKPSLMIQKAA, | (SEQ ID NO: 24) |
| IQKAAIQALRKMEPKDKDQE, | (SEQ ID NO: 25) |
| RLNGESNLRFNSSYLQGTNO, | (SEQ ID NO: 26) |
| SLNSHGLELNADILGTDKIN, | (SEQ ID NO: 27) |
| WIQNVDTKYQIRIQIQEKLQ, | (SEQ ID NO: 28) |
| TYISDWWTLAAKNLTDFAEQ, | (SEQ ID NO: 29) |
| EATLQRIYSLWEHSTKNHLQ, | (SEQ ID NO: 30) |
| ALLVPPETEEAKQVLFLDTV, | (SEQ ID NO: 31) |
| IEIGLEGKGFEPTLEALFGK, | (SEQ ID NO: 32) |
| SGASMKLTTNGRFREHNAKF, | (SEQ ID NO: 33) |
| NLIGDFEVAEKINAFRAKVH, | (SEQ ID NO: 34) |
| GHSVLTAKGMALFGEGKAEF, | (SEQ ID NO: 35) |
| FKSSVITLNTNAELFNQSDI, | (SEQ ID NO: 36) |
| FPDLGQEVALNANTKNQKIR,<br>as well as the non antibody-producing<br>peptide | (SEQ ID NO: 37) |
| ATRFKHLRKYTYNYQAQSSS, | (SEQ ID NO: 38) | or an active site of one or more of these peptides.

Material and Methods

To determine which parts of apolipoprotein B that become immunogenic as a result of LDL oxidation a polypeptide library consisting of 20 amino acid long peptides covering the complete human apolipoprotein B sequence was produced. The peptides were produced with a 5 amino acid overlap to cover all sequences at break points. Peptides were used in their native state, or after incorporation in phospholipid liposomes, after oxidization by exposure to copper or after malone dialdehyde (MDA)-modification to mimic the different modifications of the amino acids that may occur during oxidation of LDL.

Peptides

The 302 peptides corresponding to the entire human apolipoprotein B amino acid sequence were synthesized (Euro-Diagnostica AB, Malmö, Sweden and KJ Ross Petersen AS, Horsholm, Denmark) and used in ELISA. A fraction of each synthetic peptide was modified by 0.5 M MDA (Sigma-Aldrich Sweden AB, Stockholm, Sweden) for 3 h at 37° C. and in presence of liposomes by 0.5 M MDA for 3 h at 37° C. or by 5 µM $CuCl_2$ (Sigma) for 18 h at 37° C. The MDA-modified peptides were dialyzed against PBS containing 1 mM EDTA with several changes for 18 h at 4° C. The modification of the peptides was tested in denatured polyacrylamide gels (Bio-Rad Laboratories, Hercules, Calif.), suitable for separation of peptides. Peptides were numbered 1-302 starting at the N-terminal end of the protein.

Other aldehydes can be used for preparing derivatives, such hydroxynonenal and others.

Liposomes

A mixture of egg phosphatidylcholine (EPC) (Sigma) and phosphatidylserine (PS) (Sigma) in a chloroform solution at a molar ratio of 9:1 and a concentration of 3 mM phospholipid (PL) was evaporated in a glass container under gentle argon stream. The container was then placed under vacuum for 3 hours. A solution containing 0.10 mM peptide (5 ml) in sterile filtered 10 mM HEPES buffer pH 7.4, 145 mM NaCl and 0.003% sodium azide was added to the EPC/PS dried film and incubated for 15 min at 50° C. The mixture was gently vortex for about 5 min at room temperature and then placed in ice-cold water bath and sonicated with 7.5 amplitude microns for 3×3 min (Sonyprep 150 MSE Sanyo, Tamro-Medlab, Sweden) with 1 min interruptions. The PL-peptide mixture, native or modified by 0.5 M MDA for 3 h at 37° C. or 5 mM $CuCl_2$ for 18 h at 37° C., was stored under argon in glass vials at 4° C. wrapped in aluminum foil and used within 1 week. The MDA-modified mixture was dialyzed against PBS containing 1 mM EDTA with several changes for 18 h at 4° C. before storage. The modification of the mixture was tested in denatured polyacrylamide gels (Bio-Rad Laboratories AB, Sundbyberg, Sweden), suitable for separation of peptides.

Plasma Samples

Plasma samples from 10 patients with cardiovascular disease (AHP) and 50 plasma samples, 25 women and 25 men, from normal blood donors (NHP) were collected and pooled. The two pools were aliquoted and stored in −80° C.

ELISA

Native or modified synthetic peptides diluted in PBS pH 7.4 (20 µg/ml), in presence or absence of liposomes, were absorbed to microtiter plate wells (Nunc MaxiSorp, Nunc, Roskilde, Denmark) in an overnight incubation at 4° C. As a reference, one of the peptides (P6) was run on each plate. After washing with PBS containing 0.05% Tween-20 (PBS-T) the coated plates were blocked with SuperBlock in TBS (Pierce, Rockford, Il.) for 5 min at room temperature followed by an incubation of pooled human plasma, AHP or NHP, diluted 1/100 in TBS-0.05% Tween-20 (TBS-T) for 2 h at room temperature and then overnight at 4° C. After rinsing, deposition of auto-antibodies directed to the peptides were detected by using biotinylated rabbit anti-human IgG- or IgM-antibodies (Dako A/S, Glostrup, Denmark) appropriately diluted in TBS-T. After another incubation for 2 h at room temperature the plates were washed and the bound biotinylated antibodies were detected by alkaline phosphatase conjugated streptavidin (Sigma), incubated for 2 h at room temperature. The color reaction was developed by using phosphatase substrate kit (Pierce) and the absorbance at 405 nm was measured after 1 h of incubation at room temperature. The absorbance values of the different peptides were divided with the absorbance value of P6 and compared.

The sequences in apolipoprotein B that were recognized by antibodies in human plasma are shown as Seq. Id 1-37 in the accompanying drawing. Both AHP and NHP contained antibodies to a large number of different peptides. Antibodies against both native and modified peptides were identified. Generally antibody titers to MDA modified peptides were higher or equal to that of the corresponding native peptide. Comparison between native, MDA-modified, copper-oxidized peptide showed a high degree of correlation and that the highest antibody titers were detected using MDA-modified peptides. The use of peptides incorporated into liposomes did not result in increased antibody levels. Antibodies of the IgM subclass were more common than antibodies of the IgG subtype.

The peptides against which the highest antibody levels were detected could be divided into six groups with common characteristics (Table 1):
(A) High levels of IgG antibodies to MDA-modified peptides (n=3).
(B) High levels of IgM antibodies, but no difference between native and MDA-modified peptides (n=9).
(C) High levels of IgG antibodies, but no difference between native and MDA-modified peptides (n=2).
(D) High levels of IgG antibodies to MDA-modified peptides and at least twice as much antibodies in the NHP-pool as compared to the AHP-pool (n=5).
(E) High levels of IgM antibodies to MDA-modified peptides and at least twice as much antibodies in the NHP-pool as compared to the AHP-pool (n=11)
(F) High levels of IgG antibodies, but no difference between intact and MDA-modified peptides but at least twice as much antibodies in the AHP-pool as compared to the NHP-pool (n=7).
(G) No level of IgG or IgM antibodies

TABLE 1

```
A. High IgG, MDA-difference
P 11.    FLDTVYGNCSTHFTVKTRKG,    (SEQ ID NO: 1)
P 25.    PQCSTHILQWLKRVHANPLL,    (SEQ ID NO: 2)
P 74.    VISIPRLQAEARSEILAHWS,    (SEQ ID NO: 3)

B. High IgM, no MDA-difference
P 40.    KLVKEALKESQLPTVMDFRK,    (SEQ ID NO: 4)
P 68.    LKFVTQAEGAKQTEATMTFK,    (SEQ ID NO: 5)
P 94.    DGSLRHKFLDSNIKFSHVEK,    (SEQ ID NO: 6)
P 99.    KGTYGLSCQRDPNTGRLNGE,    (SEQ ID NO: 7)
P 100.   RLNGESNLRFNSSYLQGTNQ,    (SEQ ID NO: 8)
P 102.   SLTSTSDLQSGIIKNTASLK,    (SEQ ID NO: 9)
P 103.   TASLKYENYELTLKSDTNGK,    (SEQ ID NO: 10)
P 105.   DMTFSKQNALLRSEYQADYE,    (SEQ ID NO: 11)
P 177.   MKVKIIRTIDQMQNSELQWP,    (SEQ ID NO: 12)

C. High IgG, no MDA difference
P 143.   IALDDAKINFNEKLSQLQTY,    (SEQ ID NO: 13)
P 210.   KTTKQSFDLSVKAQYKKNKH,    (SEQ ID NO: 14)

D. NHS/AHP, IgG-ak > 2, MDA-difference
P1.      EEEMLENVSLVCPKDATRFK,    (SEQ ID NO: 15)
P 129.   GSTSHHLVSRKSISAALEHK,    (SEQ ID NO: 16)
P 148.   IENIDFNKSGSSTASWIQNV,    (SEQ ID NO: 17)
```

TABLE 1-continued

```
P 162.   IREVTQRLNGEIQALELPQK,    (SEQ ID NO: 18)
P 252.   EVDVLTKYSQPEDSLIPFFE,    (SEQ ID NO: 19)

E. NHS/AHP, IgM-ak > 2, MDA-difference
P 301.   HTFLIYITELLKKLQSTTVM,    (SEQ ID NO: 20)
P 30.    LLDIANYLMEQIQDDCTGDE,    (SEQ ID NO: 21)
P 31.    CTGDEDYTYKIKRVIGNMGQ,    (SEQ ID NO: 22)
P 32.    GNMGQTMEQLTPELKSSILK,    (SEQ ID NO: 23)
P 33.    SSILKCVQSTKPSLMIQKAA,    (SEQ ID NO: 24)
P 34.    IQKAAIQALRKMEPKDKDQE,    (SEQ ID NO: 25)
P 100.   RLNGESNLRFNSSYLQGTNQ,    (SEQ ID NO: 26)
P 107.   SLNSHGLELNADILGTDKIN,    (SEQ ID NO: 27)
P 149.   WIQNVDTKYQIRIQIQEKLQ,    (SEQ ID NO: 28)
P 169.   TYISDWWTLAAKNLTDFAEQ,    (SEQ ID NO: 29)
P 236.   EATLQRIYSLWEHSTKNHLQ,    (SEQ ID NO: 30)

F. NHS/AHP, IgG-ak < 0.5, no MDA-difference
P 10.    ALLVPPETEEAKQVLFLDTV,    (SEQ ID NO: 31)
P 45.    IEIGLEGKGFEPTLEALFGK,    (SEQ ID NO: 32)
P 111.   SGASMKLTTNGRFREHNAKF,    (SEQ ID NO: 33)
P 154.   NLIGDFEVAEKINAFRAKVH,    (SEQ ID NO: 34)
P 199.   GHSVLTAKGMALFGEGKAEF,    (SEQ ID NO: 35)
P 222.   FKSSVITLNTNAELFNQSDI,    (SEQ ID NO: 36)
P 240.   FPDLGQEVALNANTKNQKIR,    (SEQ ID NO: 37)

G.
P 2.     ATRFKHLRKYTYNYQAQSSS.    (SEQ ID NO: 38)
```

All of these 38 peptide sequences represent targets for immune reactions that may be of importance for the development of atherosclerosis and ischemic cardiovascular diseases. These peptides may therefore be used to develop ELISAs to determine the associations between antibody levels against defined sequences of MDA-modified amino acids in apolipoprotein B and risk for development of cardiovascular disease.

These peptides also represent possible mediators of the protective immunity observed in experimental animals immunized with oxidized LDL and may be used for testing in further development of an immunization therapy or "vaccine" against atherosclerosis.

Thus 38 different sequences in the human apolipoprotein B protein have been identified that give rise to significant immune responses in man. These epitopes are likely to represent what has previously been described as antibodies to oxidized LDL. Since most immune responses are directed against peptide sequences and apolipoprotein B is the only protein in LDL the approach used in this project should be able to identify the specific epitopes for essentially all antibodies against oxidized LDL-particles. A family of phospholipid specific antibodies including antibodies against cardiolipin has been described to react with oxidized LDL but the specificity and role of these antibodies remain to be fully characterized.

In many cases antibody titers were higher to MDA-modified polypeptides than to native sequences. If antibodies were detected against a MDA modified sequence it was almost always associated with presence of antibodies against the native sequence. A likely explanation to this is that the immune response against an MDA-modified amino acid sequence in apolipoprotein B (the MDA-modification occurring as a result of LDL oxidation) leads to a break of tolerance against the native sequence. For other sequences there was no difference in antibody titers against MDA-modified or native sequences. This would suggest that the immune reactions are directed against the native sequences. There should be no immune response against amino acid sequences in protein normally exposed to the immune system. In the native LDL particle large parts of the apolipoprotein B protein is hidden in phospholipid layer of LDL and therefore not accessible for the immune system. During oxidation of LDL the apolipoprotein B amino acid chain is fragmented leading to changes in the three-dimensional structure. This is likely to lead to exposure of peptide sequences normally not accessible for the immune system and to generation of antibodies against these sequences which may explain the presence of antibodies against native apolipoprotein B sequences observed. Alternatively, the true immune response is against MDA-modified sequences but the cross-reactivity with native sequences is so great that no difference in binding can be demonstrated.

TABLE 2

Associations between antibodies to different peptides and atherosclerosis in the carotid artery assessed as intima/media thickness in 78 subjects (26 subjects who later developed myocardial infarction, 26 healthy controls and 26 high-risk individuals without disease).

| | IgG | | IgM | |
|---|---|---|---|---|
| Peptide | Native | MDA-modified | Native | MDA-modified |
| 301 | | | | + |
| 10 | | | + | + |
| 11 | | | ++ | + |
| 25 | + | + | ++ | +++ |
| 30 | | | | ++ |
| 31 | | | ++ | ▓ |
| 32 | | | | ▓ |
| 33 | | | | + |
| 34 | | | | + |
| 45 | | ++ | ++ | +++ |
| 74 | ++ | + | + | ++ |
| 99 | | | | |
| 100 | | | + | ++ |
| 102 | | | | ▓ |
| 103 | | | + | |
| 105 | | | | |
| 129 | | | ++ | +++ |
| 143 | + | + | ++ | + |
| 148 | | | | + |
| 154 | | | +++ | ++ |
| 162 | | | + | ++ |
| 199 | | | | |
| 210 | | | + | |
| 240 | | | ++ | ▓ |

+, r > 0.2 < 0.3, p = <0.05; ++, r > 0.3 < 0.4, p = 0.01; +++, r > 0.4, p = <0.001, grey, peptide antibody levels significantly increased in the group suffering from myocardial infarction.

The possibility that the ELISAs based on these peptides (native or MDA-modified) can be used to determine associations between immune reaction against defined epitopes in oxidized LDL and presence and/or risk for development of cardio-vascular disease was investigated in a pilot study. The study was performed on subjects participating in the Malmö Diet Cancer study a population based study in which over 30,000 individuals were recruited between 1989 and 1993. Antibody levels against the 24 out of 38 peptides listed in Table 1 were determined in base line plasma samples of 26 subjects who developed an acute myocardial infarction during the follow-up period and 26 healthy controls matched for age, gender and smoking. An additional group of 26 subjects, matched for age, gender, and smoking, but all with LDL cholesterol levels above 5.0 mmol/L was also included to study antibody levels in a high-risk group that has not developed cardiovascular disease.

For 19 out of the 24 peptides analyzed, significant correlations were identified between IgM antibody levels against MDA-modified peptides and the severity of atherosclerosis in the carotid artery (intima/media thickness) as assessed by ultrasound investigation of common carotid artery, i.e., the higher antibody levels the more atherosclerosis (Table 2). For many of these peptides significant correlations also existed between antibody levels to native peptides and carotid intima/media thickness. Only 4 peptides showed a significant correlation between IgG antibodies and carotid intima/media thickness. These observations suggest that ELISA using these MDA-modified peptides (alone or in combination) may be used to identify subjects with increased atherosclerosis.

Four of the peptides tested were not only associated with increased presence of atherosclerosis but were also significant elevated in the group of subjects that later suffered from a myocardial infarction (Table 2). These observations also demonstrate that peptide-based ELISA also may be used to identify subjects with an increased risk to develop myocardial infarction.

There were also significant increases in IgG antibody levels for native peptides 103, 162 and 199, as well as MDA modified 102 in the group that later suffered from myocardial infarction. However, the IgG antibodies against these peptides were not significantly associated with the presence of atherosclerosis in the carotid artery.

A particularly interesting observation was made with antibodies against MDA-modified peptide 210 for which there was significantly higher levels of IgM antibodies in the healthy controls and the high-risk group (LDL cholesterol above 5.0 mmol/L) than in the group that developed a myocardial infarction. Accordingly antibodies against MDA-modified peptide 210 may represent a marker for individuals with a decreased risk to develop cardiovascular disease.

It has now been demonstrated that immunization with native and MDA-modified apo B-100 peptide sequences results in an inhibition of atherosclerosis in experimental animals (Nordin Fredrikson, Söderberg et al, Chyu et al). The mechanisms through which these athero-protective immune responses operate remain to be fully elucidated. However, one likely possibility is that the athero-protective effect is mediated by antibodies generated against these peptides sequences. These antibodies could, for example facilitate the removal of oxidatively damaged LDL particles by macrophage Fc receptors.

Macrophage scavenger receptors only recognize LDL with extensive oxidative damage (9). Recent studies have identified the existence of circulating oxidized LDL (10, 11). These particles have only minimal oxidative damage and are not recognized by scavenger receptors. Binding of antibodies to these circulating oxidized LDL particles may help to remove them from the circulation before they accumulate in the vascular tissue (12).

Several studies have supported a role for antibodies in protection against atherosclerosis. B cell reconstitution inhibits development of atherosclerosis in splenectomized apo E null mice (13) as well as neointima formation after carotid injury in RAG-1 mice (unpublished observations from our laboratory). Moreover, it has been shown that repeated injections of immunoglobulins reduce atherosclerosis in apo E null mice (6).

As discussed above antibodies against MDA-modified peptide sequences in apo B-100 may be generated by active immunization using synthetic peptides. This procedure requires 2-3 weeks before a full effect on antibody production is obtained.

In some situations a more rapid effect may be needed. One example may be unstable atherosclerotic plaques in which oxidized LDL is likely to contribute to inflammation, cell toxicity and risk for plaque rupture. Under these circumstances a passive immunization by injection of purified, or recombinantly produced antibodies against native and MDA-modified sequences may have a faster effect.

Another situation in which a passive immunization by injection of purified, or recombinantly produced antibodies may be effective is coronary heart disease in older individuals. Our studies have shown that a decrease in antibodies against apo B peptide sequences occurs with increasing age in man and is associated with an increase in the plasma level of oxidized LDL (Nordin Fredrikson, Hedblad et al). This may suggest a senescence of the immune cells responsible for producing antibodies against antigens in oxidized LDL and result in a defective clearance of oxidatively damaged LDL particles from the circulation. Accordingly, these subjects would benefit more from a passive immunization by injection of purified, or recombinantly produced antibodies than from an active immunization with apo B-100 peptide sequences.

Synthetic native peptides (Euro-Diagnostica AB, Malmö, Sweden) used in the following were peptide 1, 2 and 301 from the initially screened polypeptide library. Peptide 1 (amino acid sequence: EEEMLENVSLVCPKDATRFK, n=10; (SEQ ID NO: 15)) and peptide 301 (amino acid sequence: HTFLIYITELLKKLQSTTVM, n=10; (SEQ ID NO: 20)) were found to have higher IgG or IgM antibody response to MDA modified form than native peptide, respectively and both titers are higher in healthy subject. These peptides were chosen based on the assumption that antibody response to these peptides might be protective against atherosclerosis.

Peptide 2 (amino acid sequence: ATRFKHLRKY-TYNYQAQSSS, n=10; (SEQ ID NO: 38)) elicited no antibody response in the initial antibody screening, hence it was chosen as control peptide. Mice receiving Alum served as control (n=9).

Apo E (−/−) mice received subcutaneous primary immunization at 6-7 weeks of age, followed by an intra-peritoneal booster 3 weeks later. Mice were fed high cholesterol diet from the onset of immunization and continued until sacrifice at the age of 25 weeks. At the time of sacrifice, there was no significant difference in body weight among 4 groups of mice. Nor there was statistically significant difference in serum cholesterol as measured using a commercially available kit (Sigma). Their mean serum cholesterol levels were all above 715 mg/dl.

Figure 2:
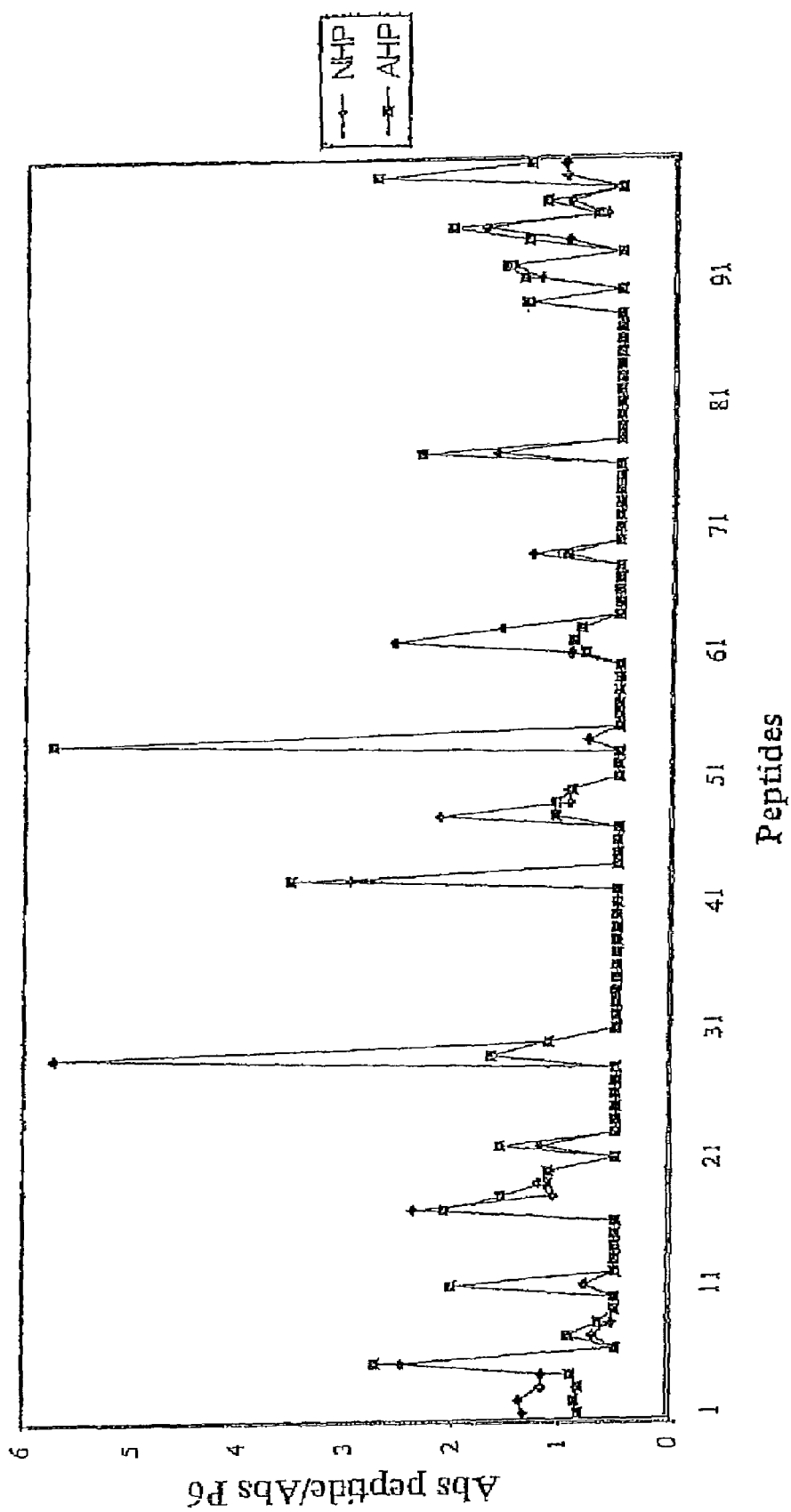
Figure 3:
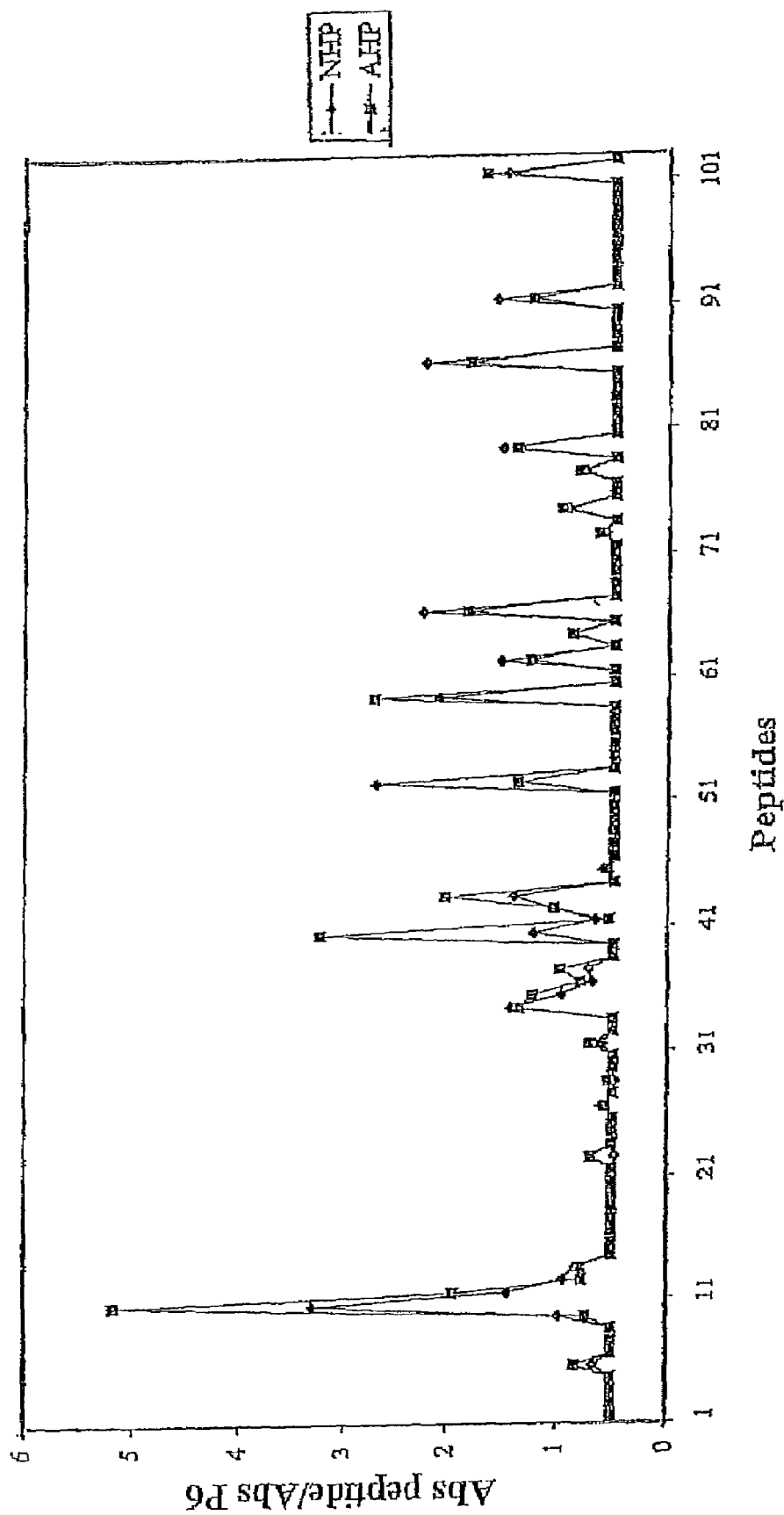
Figure 4:
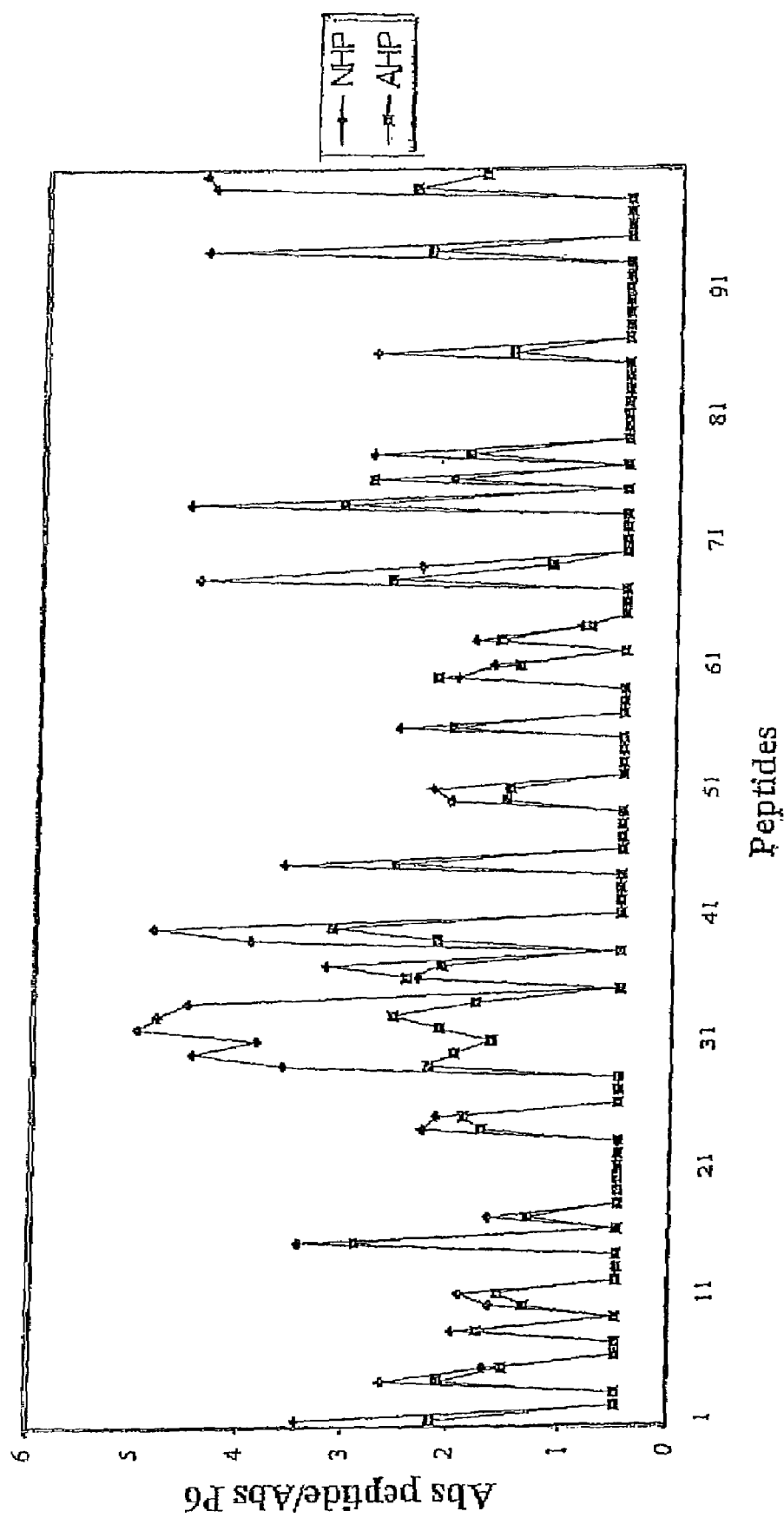
Figure 5:
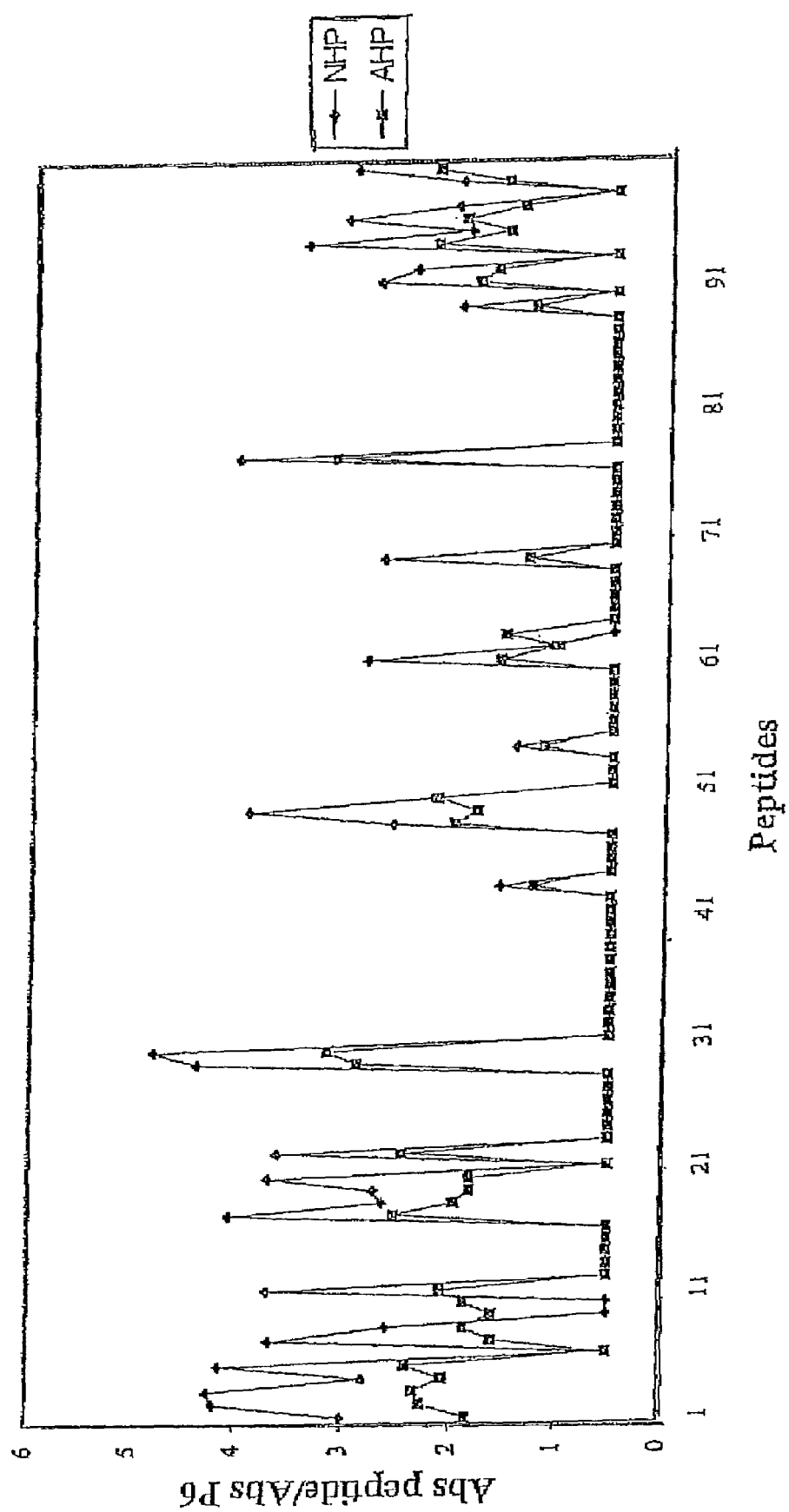
Figure 6:
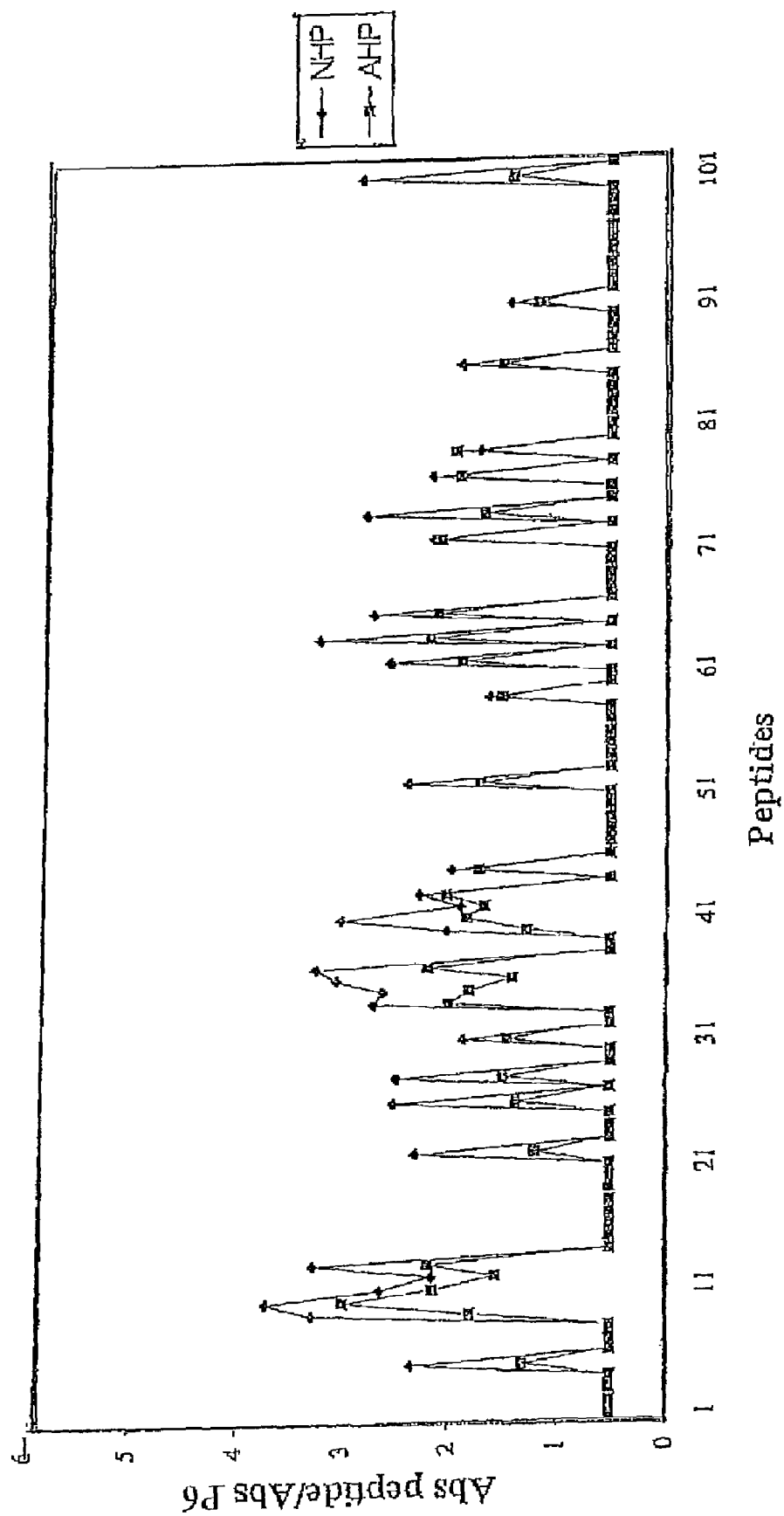

The area of the descending aorta covered by atherosclerotic plaque was measured in an en face preparation after oil red O staining. In comparison to the control group, mice immunized with peptide No. 2 and No. 301 had substantially reduced atherosclerosis (FIG. 2). Immunization with Peptide No 1 did not produce a significant reduction in atherosclerosis in comparison to control. In contrast to the descending aorta, extent of atherosclerosis in the aortic root and aortic arch did not differ among the 4 experimental groups (FIG. 3).

There were no difference among 4 groups in terms of aortic sinus plaque size or its lipid content (Table A). Mean plaque sizes in the aortic arches from 4 groups of mice were not different. However, en face evaluation of plaque sizes from descending thoracic and abdominal aorta by oil red O staining revealed that control group and peptide No. 1 group had similar amount of atherosclerotic plaque in the aorta, whereas peptide No. 2 and No. 9 groups had a significantly reduced atherosclerotic burden in the aorta (Table A). The observation that peptide immunization did not affect aortic sinus or aortic arch plaque size but reduced descending aortic plaque is intriguing and suggests that peptide immunization might reduce new plaque formation but does not affect the progression of plaques.

It was further tested whether peptide immunization modulates the phenotype of atherosclerotic plaques. Frozen sections form aortic sinus plaques were immunohistochemically stained with monocyte/macrophage antibody (MOMA-2, Serotec). In concordance with the findings from en face observation, peptide No. 2 significantly reduced macrophage infiltration in the plaques (FIG. 1). Trichrome staining revealed a mean collage content of 40.0±7.7% in the aortic sinus plaques from peptide 2 group; whereas mean collagen content in alum control group, peptide 1 group and peptide 9 group were 32.3±5.3%, 35.6±8.5% and 29.4±9.6%, respectively.

Antibody response against immunized peptide in each group was determined. Antibody titer after immunization increased 6.1±3.1 fold in peptide 1 group, 2.4±1.0 fold in peptide 2 group and 1.8±0.6 fold in peptide 9 group; whereas alum group had a 3.9±2.7 fold increase of antibody titer against peptide 1, 2.0±0.5 fold increase against peptide 2 and 2.0±0.9 fold increase against peptide 9. It is surprising the parallel increase of antibody titer against immunized peptides both in immunized and alum treated group. This may mean the following possibilities: (1) mechanism(s) other than humoral immune response (such as cellular immune response) may be involved in modulating atherosclerosis; or (2) this increase of antibody was a by-stander response to hypercholesterolemia with time.

Although there is no clear speculative mechanism to explain why peptide immunization reduced atherosclerosis and/or modulate plaque phenotype, the novelty of this invention is the concept of using peptides of LDL as immunogen and its feasibility as an immunomodulation strategy. This peptide-based immunization strategy modulates atherosclerotic plaques. Immunization using homologous oxLDL or native LDL as antigen had been shown to reduce plaque size[1-3], however, the availability, production, infectious contamination and safety of homologous human LDL make this approach unappealing for clinical application. Here it is demonstrated that peptide-based immunotherapy is feasible although our final results differ from our initial hypothesis that immunization using peptides with higher IgM or IgG antibody response in normal subjects may protect experimental animals from developing advanced atherosclerotic plaques.

It is surprising to find that immunization using peptide No. 2 protected animal from developing new atherosclerotic lesions in descending aorta and reduced macrophage infiltration and a higher collagen content in plaques since this peptide did not render any antibody response from initial human screen. It may be because (a) peptide No. 2 may be a part of human apo-B-100 protein structure that was not exposed to human immune system. Hence, no antibody was generated and detected from healthy human serum pools; (b) the amino acid sequence of peptide No. 2 is foreign to mice therefore mice developed immune response against this peptide, which modulates new atherosclerotic lesion formation and its phenotype.

The effect of homologous LDL immunization on plaque size varied when plaque sizes were evaluated at different portions of aortic tree. For example, Ameli et al showed in hypercholesterolemic rabbit native LDL immunization resulted in a reduction of plaque formation in aorta[1], whereas Freigang et al. showed reduction of plaque size in aortic sinus but not in aorta[2]. Taken their findings and the present ones together, it was speculated that peptide immunization modulates not only plaque sizes but also plaque composition. The plaque-reducing effect was only observed in descending aorta. Apo E (−/−) mice are known to develop atherosclerotic lesions at various stages of evolution in a single animal, especially when fed high cholesterol diet. The initial appearance of atherosclerotic lesion in young animal was in the aortic sinus[6,7] and after 15 weeks on high fat-high cholesterol diet lesions at aortic sinus were advanced plaques; whereas earlier stage of atherosclerosis was present in descending aorta.[6] Since the temporal course of plaque maturation and development in the descending aorta is late compared to that of aortic sinus, the finding that immunization reduced lesion sizes in the descending aorta but not in aortic sinus suggested immunization affects early stage of atherosclerosis formation. It is possible that as animal aged and in the presence of supra-physiological level of serum cholesterol the plaque reducing effect of immunization is overcome by the toxic effect of hypercholesterolemia. It is also possible that aortic sinus plaques mature faster and sacrifice at 25 weeks is too late to detect any difference in plaque size. Though lesion size was not modulated in the aortic sinus plaque, peptide immunization did modulate plaque compositions. The present experimental design prevented from studying the composition of the plaques in their earlier stage of development in descending aorta.

The experimental findings highlight the feasibility of using peptide sequences of LDL associated apo B-100 as immunogens for a novel approach to preventing atherosclerosis and or favorably modulating plaque phenotype despite severe hyperlipdemia. This peptide-based immunization strategy is potentially advantageous over the use of homologous oxLDL or native LDL as antigen because such a strategy could eliminate the need for isolation and preparation of homologous LDL and its attendant risks for contamination. The plaque-reducing effect of immunization with Peptide No 2 and 301 was only observed in descending aorta. These findings are consistent with previous reports where other therapeutic interventions have also been shown to have a greater effect on descending aorta compared to the aortic arch[14-17], presumably because lesions develop more rapidly in the aortic root and the arch than the descending aorta thus creating a smaller window of opportunity for intervention[14, 15, 16, 18, 19]. Since the temporal course of plaque maturation and development in the descending aorta is late compared to that of aortic sinus and the aortic arch, the finding that immunization reduced lesion sizes in the descending aorta but not in aortic sinus and arch suggest that immunization preferentially prevents early stage of atherosclerosis formation. It is possible that as animal aged and in the presence of supra-physiological level of serum cholesterol the plaque reducing effect of immunization is overcome by the toxic effect of severe hypercholesterolemia. Though the lesion size was not modulated in the aortic sinus or arch, immunization with Peptide No 2 did modulate plaque composition in a favorable direction creating a more stable plaque phenotype with reduced macrophage infiltration and increased collagen content. In summary, it is demonstrated a novel peptide-based immunomodulatory approach for inhibition of atherosclerosis in the murine model.

In summary, it is demonstrated a novel peptide-based immunomodulatory approach in modulate atherosclerotic plaques. Although the change in atherosclerosis formation in our model was only modest, yet this peptide-based immunization may provide an alternative tool in studying, preventing or treating atherosclerosis.

Methods

Peptide preparation. Peptides were prepared using Imject® SuperCarrier® EDC kit (Pierce, Rockford, Ill.) according to manufacturer's instruction with minor modification. One mg peptide in 500 μl conjugation buffer was mixed with 2 mg carrier in 200 μl deionized water. This mixture was then incubated with 1 mg conjugation reagent (EDC, 1-ethyl-3-[3-dimethylaminopropyl]carbodiimide HCl) in room temperature for 2 hours. This was then dialyzed against 0.083 M sodium phosphate, 0.9 M sodium chloride pH 7.2 solution overnight at 4° C. The dialyzed conjugate was diluted with Imject dry blend purification buffer to a final volume of 1.5 ml. Alum was used as immunoadjuvant and mixed with peptide conjugate with 1:1 dilution in volume. The amount of peptide in each immunization was 33 μg/100 μl per injection.

Animal protocol. Apo E (−/−) mice from the Jackson Laboratories (Bar Harbor, Me.) received subcutaneous primary immunization at 6-7 weeks of age, followed by an intraperitoneal booster 3 weeks later. Mice were fed high cholesterol diet from the onset of immunization and continued until sacrifice at the age of 25 weeks. Blood samples were collected 2 weeks after booster and at the time of sacrifice. Mice receiving Alum served as control. Experimental protocol was approved by the Institutional Animal Care and Use Committee of Cedars-Sinai Medical Center. All mice were housed in an animal facility accredited by the American Association of Accreditation of Laboratory Animal Care and kept on a 12-hour day/night cycle and had unrestricted access to water and food. At the time of sacrifice, mice were anesthetized by inhalation Enflurane. Plasma was obtained by retro-orbital bleeding prior to sacrifice.

Tissue harvesting and sectioning. To evaluate the effect of peptide immunization on atherosclerosis formation, the plaque size at aortic sinus was assessed, aortic arch and descending thoracic and abdominal aorta. After the heart and aortic tree were perfused with normal saline at physiological pressure, the heart and proximal aorta were excised and embedded in OCT compound (Tissue-Tek) and frozen sectioned. Serial 6-μm-thick sections were collected from the appearance of at least 2 aortic valves to the disappearance of the aortic valve leaflets for aortic sinus plaque evaluation. Typically 3 consecutive sections were on one slide and a total of 25-30 slides were collected from one mouse and every fifth slide was grouped for staining. Ascending aorta and aortic arches up to left subclavian artery were also sectioned and processed similarly. Descending thoracic and abdominal aorta were processed separately for en face evaluation of plaque formation after oil red O staining. En face preparation of descending thoracic and abdominal aorta Chicken egg albumin (Sigma) in a concentration of 0.8 g/ml water was mixed 1:1 with glycerol. Sodium azide was added to make a final concentration of sodium azide 0.2%. After descending thoracic and abdominal aorta was cleaned off surrounding tissue and fat, the segment of aorta from left subclavian artery to the level of renal artery was then carefully removed for overnight fixation in Histochoice (Amresco). Aorta was then carefully opened longitudinally and placed with luminal side up on a slide freshly coated with egg albumin solution. After albumin solution became dry, the aorta was stained with Oil red O to assess the extent of atherosclerosis with computer-assisted histomorphometry.

Immunohistochemistry and Histomorphometry. The sections from aortic sinus were immunohistochemically stained with MOMA-2 antibody (Serotec) using standard protocol. Trichrome stain to assess collagen content and oil red O stain for plaque size and lipid content were done using standard staining protocol. Computer-assisted morphometric analysis was performed to assess histomorphometry as described previously.[8]

Antibody titer measurement. To measure the antibody response after peptide immunization, an ELISA was developed. Antibody titer against immunized peptide was measured using blood collected at 2 weeks after booster and at sacrifice. Antibody response against 3 peptides was also determined in Alum group at the same time-points. In brief, native synthetic peptides diluted in PBS pH 7.4 (20 μg/ml) were absorbed to microtiter plate wells (Nunc MaxiSorp, Nunc, Roskilde, Denmark) in an overnight incubation at 4° C. After washing with PBS containing 0.05% Tween-20 (PBS-T) the coated plates were blocked with SuperBlock in TBS (Pierce) for 5 min at room temperature followed by an incubation of mouse serum diluted 1/50 in TBS-0.05% Tween-20 (TBS-T) for 2 h at room temperature and then overnight at 4° C. After rinsing, deposition of antibodies directed to the peptides was detected by using biotinylated rabbit anti-mouse Ig antibodies (Dako A/S, Glostrup, Denmark) appropriately diluted in TBS-T. After another incubation for 2 h at room temperature the plates were washed and the bound biotinylated antibodies were detected by alkaline phosphatase conjugated streptavidin (Sigma), incubated for 2 h at room temperature. Using phosphatase substrate kit (Pierce) developed the colour reaction and the absorbance at 405 nm was measured after 1 h of incubation at room temperature. Mean values were calculated after the background was subtracted.

Other assay models is of course applicable as well, such any immunoassay detecting an antibody, such as radioactive immunoassay, Western blotting, and Southern blotting, as well as detection of antibodies bound to peptides, enzyme electrodes and other methods for analysis.

Statistics

Data are presented as mean±Std. Statistical method used is listed in either text, table or figure legend. P<0.05 was considered as statistically significant.

TABLE A

Aortic sinus plaque size and its lipid content, aortic arch plaque size and percent of plaque in descending aorta.

|  | Total plaque size in aortic sinus (mm$^2$) | Oil red O (+) area (% of aortic sinus plaque) | Aortic arch plaque size (mm$^2$) | % of plaque in aorta (flat prep.) |
|---|---|---|---|---|
| Alum | 0.49 ± 0.13 | 21.7 ± 4.4 | 0.057 ± 0.040 | 20 ± 4.7 |
| Peptide 1 | 0.48 ± 0.14 | 32.0 ± 8.1 | 0.054 ± 0.027 | 17 ± 4.3 |
| Peptide 301 | 0.46 ± 0.16 | 23.8 ± 4.1 | 0.050 ± 0.024 | 8.9 ± 2.2* |

*Significant different from Alum group. ANOVA followed by Tukey-Kramer test was used for statistical analysis.

Further data on the effect of immunization with apolipoprotein B-100 peptide sequences on atherosclerosis in apo E knockout mice is given below in Table B

TABLE B

Effect of immunization with apolipoprotein B-100 peptide sequences on atherosclerosis in apo E knockout mice

|  | Effect on atherosclerosis in the aorta |
|---|---|
| Immunizations using mixtures of several peptide sequences | |
| 1. Peptide sequences 143 and 210 | −64.6% |
| 2. Peptide sequences 11, 25 and 74 | −59.6% |
| 3. Peptide sequences 129, 148 and 167 | −56.8% |
| 4. Peptide sequences 99, 100, 102, 103 and 105 | −40.1% |
| 5. Peptide sequences 30, 31, 32, 33 and 34 | +6.6% |
| 6. Peptide sequences 10, 45, 154, 199 and 240 | +17.8% |
| Immunizations using a single peptide sequence | |
| 1. Peptide sequence 2 | −67.7% |
| 2. Peptide sequence 210 | −57.9% |
| 3. Peptide sequence 301 | −55.2% |
| 4. Peptide sequence 45 | −47.4% |
| 5. Peptide sequence 74 | −31.0% |
| 6. Peptide sequence 1 | −15.4% |
| 7. Peptide sequence 240 | 0% |

Administration of the peptides is normally carried by injection, such as subcutaneous injection, intravenous injection, intramuscular injection or intraperitoneal injection. A first immunizing dosage can be 1 to 100 mg per patient depending on body weight, age, and other physical and medical conditions. In particular situations a local administration of a solution containing one or more of the peptides via catheter to the coronary vessels is possible as well. Oral preparations may be contemplated as well, although particular precautions must be taken to admit absorption into the blood stream. An injection dosage may contain 0.5 to 99.5% by weight of one or more of the fragments or peptides of the present invention.

The peptides are normally administered as linked to cationized bovine serum albumine, and using aluminium hydroxide as an adjuvant. Other adjuvants known in the art can be used as well.

Solutions for administration of the peptides shall not contain any EDTA or antioxidants.

The peptides can also be used as therapeutic agents in patients already suffering from an atheroschlerosis. Thus any suitable administration route can be used for adding one or more of the fragments or peptides of the invention.

Initial studies focused on determining which type of oxidative modifications of peptides led to recognition by antibodies in human plasma. These studies were done using peptides 1-5 and 297-302. During oxidation of LDL polyunsaturated fatty acids in phospholipids and cholesteryl esters undergo peroxidation leading to formation of highly reactive breakdown products, such as malone dialdehyde (MDA). MDA may then form covalent adducts with lysine and histidine residues in apo B-100 making them highly immunogenic. Oxidation of LDL also results in fragmentation of apo B-100 that may lead to exposure of peptide sequences not normally accessible for the immune system. In these experiments peptides were used in their native state, after MDA modification or after incorporation into phospholipid liposomes followed by copper oxidation or MDA-modification. IgM antibodies were identified against native, MDA- and liposome oxidized peptides, with antibody titers MDA-peptide>MDA-modified liposome peptides>liposome oxidized peptide>native peptide. Specificity testing demonstrated that binding of antibodies to MDA-modified peptides was competed by both MDA-LDL and copper oxidized LDL.

We then performed a screening of the complete peptide library using pooled plasma derived from healthy control subjects and native and MDA-modified peptides as antigens. Antibodies to a large number of sites in apo B-100 were identified. Using twice the absorbance of the background control as positive titer cut off, antibodies were detected against 102 of the 302 peptides constituting the complete apo B-100 sequence. IgM binding was substantially more abundant than that of IgG. Generally, binding was higher to MDA modified peptide sequences than to the corresponding native sequence, but these was a striking correlation between the two. Binding to both native and MDA modified sequences was competed by addition of MDA-modified LDL and copper oxidized LDL, but not by native LDL. These observations suggest that immune responses against MDA-modified peptide sequences in apo B-100 results in a cross reactivity against native sequences. The inability of native LDL to compete antibody binding to native apo B-100 peptide sequences is intriguing, but may indicate that these sequences only become exposed after the proteolytic degradation of apo B-100 that occurs as a result of LDL oxidation. Both hydrophilic and hydrophobic parts of the molecule were recognized by antibodies. A second screening of the apo B-100 peptide library was performed using pooled plasma from subjects with clinical signs of coronary heart disease (CHD, acute myocardial infarction (AMI) and unstable angina; n=10). Antibodies in pooled CHD plasma bound to the same sequences and with the same overall distribution as for antibodies in healthy control plasma. However, antibody titers to several peptides (#1, 30-34, 100, 107, 148, 149, 162, 169, 236, 252 and 301) were at least twice as high as in control plasma compared to plasma from CHD subjects, whereas titers against a few peptides (#10, 45, 111, 154, 199, 222 and 240) were higher in plasma from CHD patients compared to controls. We then performed a prospective clinical study to investigate if antibody levels against MDA-modified peptide sequences in apo B-100 predict risk for development of CHD. Using a nested case control design we selected 78 subjects with coronary events (AMI or death due to CHD) and 149 controls from the Malmö Diet Cancer Study. Neither cases nor control individuals had a history of previous MI or stroke. The median time from inclusion to the acute coronary event was 2.8 years (range 0.1-5.9 years) among cases. Antibody levels were determined in baseline plasma samples supplemented with antioxidants. Using the carotid intima-media thickness (IMT) as assessed by ultrasonography at baseline we also analyzed associations between antibody levels and degree of existing vascular disease. We studied 8 MDA-modified peptide sequences that in the initial screening studies were associated with high plasma antibody levels (#74, 102 and 210) and/or marked differences between control and CHD plasma pools (#32, 45, 129, 162 and 240). Controls were found to have higher IgM levels against MDA peptide 74 (0.258, range 0-1.123 absorbance units versus 0.178, range 0-0.732 absorbance units, p<0.05), otherwise there were no differences in antibody levels between cases and controls. Associations between IMT and IgM against MDA-peptides #102, 129, and 162 (r=0.233, 0.232, and 0.234, respectively, p<0.05) were observed in cases and between IMT and MDA-peptide 45 (r=0.18, p<0.05) in controls. Weak correlations were observed between antibodies to MDA peptide 129 and total and LDL cholesterol (r=0.19 and r=0.19, p<0.01, respectively), otherwise peptide antibody levels showed no associations with total plasma cholesterol, LDL cholesterol, HDL cholesterol or plasma triglycerides. There were strong co-variations between antibody levels to the different peptides (r values ranging from 0.6 to 0.9). The only exception was antibodies against MDA-peptide 74 that were weakly or not at all related to antibodies against the other peptides.

Antibodies against all sequences except MDA-peptide 74 was inversely associated with age among cases (r values ranging from −0.38 to −0.58, p<0.010.001), but not in controls. Plasma levels of oxidized LDL, in contrast, increased with age. Again this association was stronger in cases than in controls. To investigate if the associations between immune responses against MDA-modified peptide sequences and cardiovascular disease were different in different age groups a subgroup analysis was performed on cases and controls under and above the median age (61 years). In the younger age group cases had increased antibody levels against peptides 32 and 45 and decreased antibody levels against peptide 74 as compared to controls, whereas no differences were seen in the older age group. Antibodies against all MDA peptide sequences, except peptide 74, were significantly associated with IMT in the younger age group, but not in the older (Table).

These studies identify a number of MDA-modified sequences in apo B-100 that are recognized by human antibodies. MDA-modification of apo B-100 occurs as a result of LDL oxidation indicating that these antibodies belong to the family of previously described oxidized LDL autoantibodies. This notion is also supported by the observation that antibody binding to MDA-modified apo B-100 peptides is competed by addition of oxidized LDL. Together with the oxidized phospholipids identified by Hörkkö et al, these MDA-modified peptide sequences are likely to constitute the large majority of antigenic structures in oxidized LDL. In similarity with the oxidized LDL antiphospholipid antibodies, antibodies against MDA-modified apo B-100 sequences were of IgM type. This may suggest that also the latter antibodies belong to the family of T 15 natural antibodies. T 15 antibodies have been attributed an important role in the early, T cell independent defence against bacterial infections as well as in the removal of apoptotic cells. It remains to be determined if the MDA-peptide antibodies described here have similar functions. Antibodies were also identified against a large number of native apo B-100 sequences. However, the striking co-variation between antibodies to native and MDA-modified sequences suggests that also these antibodies are formed in response to LDL oxidation. It is also possible that antibodies against an MDA-modified peptide sequence cross reacts with the corresponding native sequence. If antibodies against native apo B-100 sequences bind also to native LDL particles this is likely to have a major influence on LDL metabolism. However, the finding that native LDL does not compete antibody binding to native apo B-100 sequences, as well as the lack of correlation between antibodies against native apo B-100 sequences and LDL cholesterol levels against the existence of such a phenomena.

Antibodies against MDA-modified peptide sequences decreased progressively with age in the cases, but not in the controls. With the exception of MDA-peptide 74, IgM antibodies against MDA-peptides were significantly associated with carotid IMT in the younger age group (below 62 years), but not in the older age group. These findings suggest that significant changes in the interactions between the immune system and the atherosclerotic vascular wall takes place between ages 50 and 70 years. One possibility is that in younger individuals the atherosclerotic disease process is at a more active stage with a more prominent involvement of immune cells. Another possibility is that the decreased levels of antibodies against MDA-modified peptide sequences in older subjects reflect a senescence of the immune cells involved in atherosclerosis. An impaired function of immune cells due to immunosenescence have been proposed to contribute to an increased susceptibility to infection and cancer in the older population. Interestingly, immunosenescence is inhibited by antioxidants indicating involvement of oxidative stress. Immune cells that interact with epitopes in oxidized LDL are likely to be particularly exposed to oxidative stress. Since oxidized LDL is present in arteries already at a very early age these immune response are being continuously challenged for several decades, which may further contribute to a development of immunosenescence.

Increased antibodies against two sites in apo B-100 were found to predict risk for myocardial infarction and coronary death in subjects below 62 years of age. Antibodies against these sites showed a high level of co-variation suggesting that they were produced in response to the same underlying pathophysiological processes. The fact that the median time from blood sampling to coronary event was only 2.8 years makes these antibodies particularly interesting as makers for increased CHD risk. Antibody levels against MDA-modified apo B-100 peptide sequences showed no associations with other CHD risk factors such as hyperlipidemia, hypertension and diabetes suggesting that they are independent markers of CHD risk. The CHD cases in the present study were not extremely high-risk individuals and in this respect representative of the common CHD patient. The finding that IgM against MDA-modified apo B-100 sequences predicts short-term risk for development of acute coronary events in individuals that would not have been identified as high risk by screening of established risk factors suggest that it may become a useful instrument in identifying individuals in need of aggressive preventive treatment. However, considerably larger prospective studies with multivariate analysis are required before the clinical value of determining antibodies against apo B-100 MDA-modified peptide sequences can be fully established. Another limitation of the present clinical study is that we have only analysed antibodies against a small number of the antigenic sites in apo B-100 and that antibody titers against other sites may be even better markers of cardiovascular risk.

In subjects below age 60 antibodies against a large number of MDA-modified sites in apo B-100 were correlated with the extent of existing vascular disease as assessed by carotid IMT. IgM antibodies were more closely associated with carotid IMT than IgG antibodies. Although carotid IMT has obvious limitations as a measure of general atherosclerotic burden these observations still suggest that determination of IgM against MDA-modified sequences in apo B-100 may be one method to assess the severity of existing atherosclerosis. These observations are also in line with several previous studies that have reported associations between coronary and carotid artery disease and IgM antibodies against oxidized LDL.

Antibodies against peptide 74 differed against other apo B-100 peptide antibodies in many respect. They were higher in controls than in cases, they did not decrease with age and were not associated with the extent of carotid disease. Accordingly, antibodies against this peptide sequence represent interesting candidates for an athero-protective immune response.

An important question is why these associations occur. They clearly demonstrate that immune responses against MDA-modified apo B-100 sites somehow are involved in the atherosclerosic disease process. Since high antibody levels are associated with more severe atherosclerosis and increased risk for development of acute coronary events one obvious possibility is that these immune responses promote atherogenesis. Studies demonstrating that immune responses against heat shock proteins, such as HSP 65, are atherogenic provide some support for this notion. However, experimental animal studies have shown an athero-protective effect of oxidized LDL immunization. B cell reconstitution of spleen ectomized apo E null mice results in a decrease in atherosclerosis. Reduced atherosclerosis has also been observed in apo E null mice given repeated injections of immunoglobulin. The present observations do not necessarily argue against an athero-protective role of immune responses against oxidized LDL. These immune responses are activated by pro-atherogenic processes such as LDL oxidation. Accordingly, they are also likely to be in proportion to the severity of the disease process and could serve as makers of disease severity and CHD risk without contributing to disease progression. The finding that immunization of apo E null mice with apo B-100 peptide sequences inhibits development of atherosclerosis reported in two accompanying papers demonstrates that this is likely to be the case. Indeed, the most important outcome of the present study may well be the identification of structures that could be used as components of a vaccine against atherosclerosis. The observation that the decrease in antibodies against MDA-modified peptide sequences in apo B-100 that occurs with age is accompanied by an increase in plasma levels of oxidized LDL suggest that an increased clearance of minimally oxidized LDL from the circulation may be one mechanism by which these antibodies could protect against atherosclerosis.

Methods

Study Population

The study subjects, borr between 1926-45, belong to the Malmö "Diet and Cancer (MDC)" study cohort. A random 50% of those who entered the MDC study between November 1991 and February 1994 were invited to take part in a study on the epidemiology of carotid artery disease. Routines for ascertainment of information on morbidity and mortality following the health examination, as well as definition of traditional risk factors, have been reported.

Eighty-five cases of acute coronary heart events, i.e. fatal or non-fatal MI or deaths due to coronary heart disease (CHD) were identified. Participants who had a history of myocardial infarction or stroke (n=6) were not eligible for the present study. For each case two controls without a history of myocardial infarction or stroke was individually matched for age, sex, smoking habits, presence of hypertension and month of participation in the screening examination and duration of follow-up. Due to logistic reason (blood samples were not available in sufficient quantity for assessment of peptides) only one control was available for seven cases and no controls for one case. This case was excluded from analysis. Thus the study population consists of 227 subjects, 78 cases and 149 controls, aged 49-67 (median 61) years at baseline.

Laboratory Analyses

After overnight fasting blood samples were drawn for the determination of serum values of total cholesterol, triglycerides, HDL cholesterol, LDL cholesterol and whole blood glucose. LDL cholesterol in mmol/L was calculated according to the Friedewald formula. Oxidized LDL was measured by ELISA (Mercordia).

B-Mode Ultrasound Vasculography

An Acuson 128 Computed Tomography System (Acuson, Mountain View, Calif.) with a MHz transducer was used for the assessment of carotid plaques in the right carotid artery as described previously.

Development of ELISAs Against Apo B-100 Peptide Sequences

The 302 peptides corresponding to the entire human apolipoprotein B amino acid sequence were synthesized (Euro-Diagnostica AB, Malmö, Sweden and KJ Ross Petersen AS, Horsholm, Denmark) and used in ELISA. A fraction of each synthetic peptide was modified by 0.5 M MDA (Sigma-Aldrich Sweden AB, Stockholm, Sweden) for 3 h at 37° C. and in presence of liposomes by 0.5 M MDA for 3 h at 37° C. or by 5 mM $CUCl_2$ (Sigma) for 18 h at 37° C. The MDA modified peptides were dialysed against PBS containing 1 mM EDTA with several changes for 18 h at 4° C. The modification of the peptides was tested in denatured polyacrylamide gels (Bio-Rad Laboratories, Hercules, Calif.), suitable for separation of peptides.

A mixture of egg phosphatidylcholine (EPC) (Sigma) and phosphatidylserine (PS) (Sigma) in a chloroform solution at a molar ratio of 9:1 and a concentration of 3 mM phospholipid (PL) was evaporated in a glass container under gentle argon stream. The container was then placed under vacuum for 3 hours. A solution containing 0.10 mM peptide (5 ml) in sterile filtered 10 mM HEPES buffer pH 7.4, 145 mM NaCl and 0.003% sodium azide was added to the EPC/PS dried film and incubated for 15 min at 50° C. The mixture was gently vortex for about 5 min at room temperature and then placed in ice-cold water bath and sonicated with 7.5 amplitude microns for 3×3 min (Sonyprep 150 MSE Sanyo, Tamro-Medlab, Sweden) with 1 min interruptions. The PL-peptide mixture, native or modified by 0.5 M MDA for 311 at 37° C. or 5 mM $CUCl_2$ for 18 h at 37° C., was stored under argon in glass vials at 4° C. wrapped in aluminum foil and used within 1 week. The MDA-modified mixture was dialyzed against PBS containing 1 mM EDTA with several changes for 18 h at 4° C. before storage. The modification of the mixture was tested in denatured polyacrylamide gels (BioRad Laboratories AB; Sundbyberg, SE), suitable for separation of peptides.

Native or modified synthetic peptides diluted in PBS pH 7.4 (20 leg/ml), in presence or absence of liposomes, were absorbed to microtiter plate wells (Nunc MaxiSorp, Nunc, Roskilde, Denmark) in an overnight incubation at 4° C. As a reference, one of the peptides (P6) was ran on each plate. After washing with PBS containing 0.05% Tween-20 (PBS-T) the coated plates were blocked with SuperBlock in TBS (Pierce, Rockford, Ill.) for 5 min at room temperature followed by an incubation of pooled human plasma, diluted 1/100 in TBS-0.05% Tween-20 (TBS-T) for 2 h at room temperature and then overnight at 4° C. After rinsing, deposition of auto-antibodies directed to the peptides were detected by using biotinylated rabbit anti-human IgG- or IgM-antibodies (Dako A/S, Glostrup, Denmark) appropriately diluted in TBS-T. After another incubation for 2 h at room temperature the plates were washed and the bound biotinylated antibodies were detected by alkaline phosphatase conjugated streptavidin (Sigma), incubated for 2 h at room temperature. The color reaction was developed by using phosphatase substrate kit (Pierce) and the absorbance at 405 nm was measured after 1 h of incubation at room temperature. The absorbance values of the different peptides were divided with the absorbance value of P6 and compared.

Statistics

SPSS was used for the statistical analyses. The results are presented as median and range and as proportions when appropriate. Boxplot and scatterplots were used till illustrate the relationship between age and selected peptides among cases and corresponding controls. Corresponding graphs were also used to illustrate the relationship between age and selected peptides, cases and controls, respectively, below and above the median age (61 year) at baseline and separately for cases and controls below the median age. In cases and controls, separately, partial correlation coefficients, adjusted for age and sex, were computed between selected peptides and blood lipid levels and common carotid IMT. Age- and sex adjusted partial correlation coefficients were also computed between common carotid IMT and selected peptides in cases and controls below and over the median age. An independent sample t-test was used to assess normally distributed continuous variables and a Chi-square test for proportions between cases and controls. Non-parametric test (Mann-Whitney) was used to assess non-normally distributed continuous variables between cases and controls. All p-values are two-tailed.

TABLE

Age- and sex adjusted correlation coefficient for different baseline MDA peptides and common carotid artery intima-media thickness among younger (49-61 years) and older (62-67 years) cases with myocardial infarction and their corresponding controls matched for age, sex, smoking and hypertension.

| PEPTIDE | CASES plus CONTROLS Aged 49-61 year, n = 116 | CASES plus CONTROLS Aged 62-67 year, n = 111 |
|---|---|---|
| IGM | | |
| MDA 32 | 0.235† | -0.101 |
| MDA 45 | 0.366$ | -0.030 |
| MDA 74 | 0.178 | 0.063 |
| MDA 102 | 0.255$ | -0.039 |
| MDA 129 | 0.330$ | -0.009 |
| MDA 162 | 0.2451 | 0.001 |
| MDA 210 | 0.254 | 0.013 |
| MDA 240 | 0.284$ | 0.006 |
| IGG | | |
| MDA 215 | 0.119 | -0.059 |

$p < 0.05$;
$/x0.01

We claim:

1. A purified or recombinantly produced antibody against a fragment of apo-lipoprotein B, wherein the fragment is HTFLIYITELLKKLQSTTVM (SEQ ID NO:20).

2. The antibody according to claim 1, wherein the fragment is native or in oxidized form.

3. The antibody according to claim 2, wherein the fragment is an aldehyde-derivative.

4. The antibody according to claim 3, wherein the fragment is modified using malone dialdehyde or hydroxynonenal.

5. The antibody according to claim 3, wherein the fragment is a hapten of an aldehyde.

6. The antibody according to claim 2, wherein the fragment has been oxidized using copper.

7. The antibody according to claim 1, wherein the fragment is present in a combination with phospholipid liposomes.

8. A pharmaceutical preparation for therapeutic treatment of a mammal suffering from atherosclerosis, comprising a therapeutically effective amount of the purified or recombinantly produced antibody of claim 1.

9. A method of therapeutic treatment of a mammal suffering from atherosclerosis, comprising administering to said mammal a therapeutically effective amount of the purified or recombinantly produced antibody of claim 1.

10. The pharmaceutical preparation of claim 8, wherein the mammal is a human being.

11. The method of claim 9, wherein the mammal is a human being.

* * * * *

SEQUENCE LISTING

<160> NUMBER OF SEQ ID NOS: 38

<210> SEQ ID NO 1
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Phe Leu Asp Thr Val Tyr Gly Asn Cys Ser Thr His Phe Thr Val Lys
 1               5                  10                  15

Thr Arg Lys Gly
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Gln Cys Ser Thr His Ile Leu Gln Trp Leu Lys Arg Val His Ala
 1               5                  10                  15

Asn Pro Leu Leu
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ile Ser Ile Pro Arg Leu Gln Ala Glu Ala Arg Ser Glu Ile Leu
 1               5                  10                  15

Ala His Trp Ser
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Val Lys Glu Ala Leu Lys Glu Ser Gln Leu Pro Thr Val Met
 1               5                  10                  15

Asp Phe Arg Lys
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Lys Phe Val Thr Gln Ala Glu Gly Ala Lys Gln Thr Glu Ala Thr
 1               5                  10                  15

Met Thr Phe Lys
            20
```

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Gly Ser Leu Arg His Lys Phe Leu Asp Ser Asn Ile Lys Phe Ser
 1               5                  10                  15

His Val Glu Lys
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Gly Thr Tyr Gly Leu Ser Cys Gln Arg Asp Pro Asn Thr Gly Arg
 1               5                  10                  15

Leu Asn Gly Glu
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Leu Asn Gly Glu Ser Asn Leu Arg Phe Asn Ser Ser Tyr Leu Gln
 1               5                  10                  15

Gly Thr Asn Gln
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Leu Thr Ser Thr Ser Asp Leu Gln Ser Gly Ile Ile Lys Asn Thr
 1               5                  10                  15

Ala Ser Leu Lys
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ala Ser Leu Lys Tyr Glu Asn Tyr Glu Leu Thr Leu Lys Ser Asp
1               5                   10                  15

Thr Asn Gly Lys
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Met Thr Phe Ser Lys Gln Asn Ala Leu Leu Arg Ser Glu Tyr Gln
1               5                   10                  15

Ala Asp Tyr Glu
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Lys Val Lys Ile Ile Arg Thr Ile Asp Gln Met Gln Asn Ser Glu
1               5                   10                  15

Leu Gln Trp Pro
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Ala Leu Asp Asp Ala Lys Ile Asn Phe Asn Glu Lys Leu Ser Gln
1               5                   10                  15

Leu Gln Thr Tyr
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Thr Thr Lys Gln Ser Phe Asp Leu Ser Val Lys Ala Gln Tyr Lys
1               5                   10                  15

Lys Asn Lys His
            20

<210> SEQ ID NO 15
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 15

Glu Glu Glu Met Leu Glu Asn Val Ser Leu Val Cys Pro Lys Asp Ala
 1               5                  10                  15

Thr Arg Phe Lys
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ser Thr Ser His His Leu Val Ser Arg Lys Ser Ile Ser Ala Ala
 1               5                  10                  15

Leu Glu His Lys
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Glu Asn Ile Asp Phe Asn Lys Ser Gly Ser Ser Thr Ala Ser Trp
 1               5                  10                  15

Ile Gln Asn Val
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Arg Glu Val Thr Gln Arg Leu Asn Gly Glu Ile Gln Ala Leu Glu
 1               5                  10                  15

Leu Pro Gln Lys
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Asp Val Leu Thr Lys Tyr Ser Gln Pro Glu Asp Ser Leu Ile
 1               5                  10                  15

Pro Phe Phe Glu
```

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

His Thr Phe Leu Ile Tyr Ile Thr Glu Leu Leu Lys Lys Leu Gln Ser
1               5                   10                  15
Thr Thr Val Met
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Leu Leu Asp Ile Ala Asn Tyr Leu Met Glu Gln Ile Gln Asp Asp Cys
1               5                   10                  15
Thr Gly Asp Glu
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Cys Thr Gly Asp Glu Asp Tyr Thr Tyr Lys Ile Lys Arg Val Ile Gly
1               5                   10                  15
Asn Met Gly Gln
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Gly Asn Met Gly Gln Thr Met Glu Gln Leu Thr Pro Glu Leu Lys Ser
1               5                   10                  15
Ser Ile Leu Lys
            20

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 24

Ser Ser Ile Leu Lys Cys Val Gln Ser Thr Lys Pro Ser Leu Met Ile
1               5                   10                  15

Gln Lys Ala Ala
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Gln Lys Ala Ala Ile Gln Ala Leu Arg Lys Met Glu Pro Lys Asp
1               5                   10                  15

Lys Asp Gln Glu
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Leu Asn Gly Glu Ser Asn Leu Arg Phe Asn Ser Ser Tyr Leu Gln
1               5                   10                  15

Gly Thr Asn Gln
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Leu Asn Ser His Gly Leu Glu Leu Asn Ala Asp Ile Leu Gly Thr
1               5                   10                  15

Asp Lys Ile Asn
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Ile Gln Asn Val Asp Thr Lys Tyr Gln Ile Arg Ile Gln Ile Gln
1               5                   10                  15

Glu Lys Leu Gln
            20

<210> SEQ ID NO 29
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Tyr Ile Ser Asp Trp Trp Thr Leu Ala Ala Lys Asn Leu Thr Asp
 1               5                  10                  15

Phe Ala Glu Gln
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Ala Thr Leu Gln Arg Ile Tyr Ser Leu Trp Glu His Ser Thr Lys
 1               5                  10                  15

Asn His Leu Gln
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Leu Leu Val Pro Pro Glu Thr Glu Glu Ala Lys Gln Val Leu Phe
 1               5                  10                  15

Leu Asp Thr Val
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Glu Ile Gly Leu Glu Gly Lys Gly Phe Glu Pro Thr Leu Glu Ala
 1               5                  10                  15

Leu Phe Gly Lys
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gly Ala Ser Met Lys Leu Thr Thr Asn Gly Arg Phe Arg Glu His
 1               5                  10                  15
```

Asn Ala Lys Phe
        20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Leu Ile Gly Asp Phe Glu Val Ala Glu Lys Ile Asn Ala Phe Arg
 1               5                  10                  15

Ala Lys Val His
        20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly His Ser Val Leu Thr Ala Lys Gly Met Ala Leu Phe Gly Glu Gly
 1               5                  10                  15

Lys Ala Glu Phe
        20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Lys Ser Ser Val Ile Thr Leu Asn Thr Asn Ala Glu Leu Phe Asn
 1               5                  10                  15

Gln Ser Asp Ile
        20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Pro Asp Leu Gly Gln Glu Val Ala Leu Asn Ala Asn Thr Lys Asn
 1               5                  10                  15

Gln Lys Ile Arg
        20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 38

Ala Thr Arg Phe Lys His Leu Arg Lys Tyr Thr Tyr Asn Tyr Gln Ala
 1               5                  10                  15

Gln Ser Ser Ser
            20
```